United States Patent
Lee et al.

(10) Patent No.: US 10,138,495 B2
(45) Date of Patent: Nov. 27, 2018

(54) BIO-PRODUCTION OF LENTIVIRAL VECTORS

(71) Applicant: Calimmune, Inc., Tucson, AZ (US)

(72) Inventors: Chi-Lin Lee, Arcadia, CA (US); Jeffrey S Bartlett, Columbus, OH (US)

(73) Assignee: Calimmune, Inc., Tucson, AZ (US)

( * ) Notice: Subject to any disclaimer, the term of this patent is extended or adjusted under 35 U.S.C. 154(b) by 0 days.

(21) Appl. No.: 15/802,363

(22) Filed: Nov. 2, 2017

(65) Prior Publication Data

US 2018/0112233 A1 Apr. 26, 2018

Related U.S. Application Data

(63) Continuation of application No. PCT/US2016/031959, filed on May 12, 2016.

(60) Provisional application No. 62/161,133, filed on May 13, 2015, provisional application No. 62/161,152, filed on May 13, 2015.

(51) Int. Cl.
| | |
|---|---|
| C07H 21/02 | (2006.01) |
| C12N 15/00 | (2006.01) |
| C12N 15/86 | (2006.01) |
| A01K 67/00 | (2006.01) |

(52) U.S. Cl.
CPC .......... *C12N 15/86* (2013.01); *C12N 2310/14* (2013.01); *C12N 2310/531* (2013.01); *C12N 2740/15043* (2013.01); *C12N 2740/16041* (2013.01); *C12N 2740/16043* (2013.01); *C12N 2740/16052* (2013.01); *C12N 2800/107* (2013.01); *C12N 2800/70* (2013.01); *C12N 2830/006* (2013.01); *C12N 2830/40* (2013.01)

(58) Field of Classification Search
CPC .......... C12N 15/86; C12N 2740/16041; C12N 2740/16043; C12N 2740/16052; C12N 2740/15043; C12N 2830/40; C12N 2830/006; C12N 2310/14; C12N 2310/531

See application file for complete search history.

(56) References Cited

U.S. PATENT DOCUMENTS

| 8,912,315 | B2* | 12/2014 | Hirai et al. |
| 9,402,865 | B2* | 8/2016 | Powell et al. |
| 2012/0021950 | A1* | 1/2012 | Greiner-Stoeffele et al. |
| 2012/0201794 | A1 | 8/2012 | Chen et al. |

FOREIGN PATENT DOCUMENTS

| WO | 2011008348 A2 | 1/2011 |
| WO | 2014200557 A1 | 12/2014 |

OTHER PUBLICATIONS

Barbara Maria Guarino: "HIV-derived lentiviral vectors engineered for regulated transgene expression", Diss., Naturwissenschaften, Eidgenössische Technische Hochschule Eth Zürich, NR. 16186, 2005, Jan. 1, 2005 (Jan. 1, 2005), Zurich, XP055288610.
Orit Wolstein et al., Preclinical safety and efficacy of an anti-HIV-1 lentiviral vector containing a short hairpin RNA to CCR5 and the C46 fusion inhibitor, Methods & clinical development, vol. 1, pp. 11-11, Dec. 31, 2013.
Robert E. Throm et a., Efficient construction of producer cell lines for a SIN lentiviral vector for SCID-X1 gene therapy by concatemeric array transfection, Blood, Issue: 21, vol. 113, pp. 5104-5110, May 20, 2009.
Matthew Wielgosz et al., Generation of a lentiviral vector producer cell clone for human Wiskott-Aldrich syndrome gene therapy, Molecular therapy. Methods & clinical development, vol. 2, pp. 14063-14063, Dec. 31, 2014.
Chi-Lin Lee et al.,onstruction of stable producer cells to make high-titer lentiviral vectors for dendritic cell-based vaccination, Biotechnology and Bioengineering, Issue: 6, vol. 109, pp. 1551-1560, Jan. 5, 2012.
Anna Stornaiuolo et al., RD2-MolPack-Chim3, a Packaging Cell Line for Stable Production of Lentiviral Vectors for Anti-HIV Gene Therapy, Human Gene Therapy Methods, Issue: 4, vol. 24, pp. 228-240, Jan. 7, 2013.
Michael R. Greene et al., Transduction of human CD34+ repopulating cells with a self-inactivating lentiviral vector for SCID-X1 produced at clinical scale by a stable cell line, Human Gene Therapy Methods, Issue: 5, vol. 23, pp. 297-308, Jan. 9, 2012.
Manfred Gossen et al., Tight control of gene expression in mammalian cells by tetracycline-responsive promoters, Proceedings of the National Academy of Sciences of the United States of America, Issue: 21, vol. 93, pp. 11400-11406, Oct. 14, 1996.
J K Rose et al., Nucleotide sequences of the mRNA's encoding the vesicular stomatitis virus G and M proteins determined from cDNA clones containing the complete coding regions, Journal of Virology, Issue: 2, vol. 39, pp. 519-528, Jul. 31, 1981.
D. Lindemann et al., Versatile retrovirus vector systems for regulated gene expression in vitro and in vivo, Molecular Medicine, Issue: 7, vol. 3, pp. 466-476, Jun. 30, 1997.
Daniel S. Ory et al., A stable human-derived packaging cell line for production of high titer retrovirus/vesicular stomatitis virus G pseudotypes, Proceedings of the National Academy of Sciences of the United States of America, Issue: 21, vol. 93, pp. 11400-11406, Oct. 14, 1996.

* cited by examiner

*Primary Examiner* — Quang Nguyen
(74) *Attorney, Agent, or Firm* — Charney IP Law LLC; Thomas Finetti

(57) ABSTRACT

The present disclosure provides a method of generating a stable producer cell line. The generation of stable producer cell lines, such as those provided in accordance with the present invention, increases the reproducibility and ease of creating high titer lentiviral stocks while easing biosafety concerns and the variation in expressed envelope proteins defines the tropism of the generated virus. The present disclosure also provides for a novel lentiviral transfer vector plasmid.

12 Claims, 21 Drawing Sheets

Specification includes a Sequence Listing.

SEQUENCE LISTING

```
<160> NUMBER OF SEQ ID NOS: 15

<210> SEQ ID NO 1
<211> LENGTH: 6565
<212> TYPE: DNA
<213> ORGANISM: Artificial Sequence
<220> FEATURE:
<223> OTHER INFORMATION: Synthetic: PUC57-TL20C
```

<400> SEQUENCE: 1

```
ggccgcctcg gccaaacagc ccttgagttt accactccct atcagtgata gagaaaagtg      60
aaagtcgagt ttaccactcc ctatcagtga tagagaaaag tgaaagtcga gtttaccact     120
ccctatcagt gatagagaaa agtgaaagtc gagtttacca ctccctatca gtgatagaga     180
aaagtgaaag tcgagtttac cagtccctat cagtgataga gaaaagtgaa agtcgagttt     240
accactccct atcagtgata gagaaaagtg aaagtcgagt ttaccactcc ctatcagtga     300
tagagaaaag tgaaagtcga gctcgccatg ggaggcgtgg cctgggcggg actggggagt     360
ggcgagccct cagatcctgc atataagcag ctgcttttg cctgtactgg gtctctctgg      420
ttagaccaga tctgagcctg ggagctctct ggctaactag gaacccact gcttaagcct      480
caataaagct tgccttgagt gcttcaagta gtgtgtgccc gtctgttgtg tgactctggt     540
aactagagat ccctcagacc cttttagtca gtgtggaaaa tctctagcag tggcgcccga     600
acagggactt gaaagcgaaa gggaaaccag aggagctctc tcgacgcagg actcggcttg     660
ctgaagcgcg cacggcaaga ggcgaggggc ggcgactggt gagtacgcca aaaattttga     720
ctagcggagg ctagaaggag agagatgggt gcgagagcgt cagtattaag cggggggagaa    780
ttagatcgcg atgggaaaaa attcggttaa ggccaggggg aaagaaaaaa tataaattaa     840
aacatatagt atgggcaagc agggagctag aacgattcgc agttaatact ggcctgttag     900
aaacatcaga aggctgtaga caaatactgg gacagctaca accatccctt cagacaggat     960
cagaagaact tagatcatta tataatacag tagcaaccct ctattgtgtg catcaaagga    1020
tagagataaa agacaccaag gaagctttag acaagataga ggaagagcaa acaaaagta     1080
agaaaaaagc acagcaagca gcaggatctt cagacctgga aattccctac aatcccccaaa   1140
gtcaaggagt agtagaatct atgaataaag aattaaagaa aattatagga caggtaagag    1200
atcaggctga acatcttaag acagcagtac aaatggcagt attcatccac aattttaaaa    1260
gaaaagggg gattgggggg tacagtgcag gggaaagaat agtagacata atagcaacag     1320
acatacaaac taaagaatta caaaaacaaa ttacaaaaat tcaaaatttt cgggttttatt   1380
acagggacag cagaaatcca ctttggaaag gaccagcaaa gctcctctgg aaaggtgaag    1440
gggcagtagt aatacaagat aatagtgaca taaaagtagt gccaagaaga aaagcaaaga   1500
tcattaggga ttatgaaaaa cagatggcag gtgatgattg tgtggcaagt agacaggatg    1560
aggattagaa catggaaaag tttagtaaaa caccataagg aggagatatg agggacaatt    1620
ggagaagtga attatataaa tataaagtag taaaaattga accattagga gtagcaccca    1680
ccaaggcaaa gagaagagtg gtgcagagag aaaaaagagc agtgggaata ggagctttgt    1740
tccttgggtt cttgggagca gcaggaagca ctatgggcgc agcgtcaatg acgctgacgg    1800
tacaggccag acaattattg tctggtatag tgcagcagca gaacaatttg ctgagggcta    1860
ttgaggcgca acagcatctg ttgcaactca gtctggggg catcaagcag ctccaggcaa     1920
gaatcctggc tgtggaaaga tacctaaagg atcaacagct cctggggatt tggggttgct    1980
ctggaaaact catttgcacc actgctgtgc cttggaatgc tagttggagt aataaatctc    2040
tggaacagat ttggaatcac acgacctgga tggagtggga cagagaaatt aacaattaca    2100
caagcttaat acactcctta attgaagaat cgcaaaacca gcaagaaaag aatgaacaag    2160
aattattgga attagataaa tgggcaagtt tgtggaattg gtttaacata acaaattggc    2220
tgtggtatat aaaattattc ataatgatag taggaggctt ggtaggttta agaatagttt    2280
tgctgtgtact ttctatagtg aatagagtta ggcagggata ttcaccatta tcgtttcaga   2340
```

```
cccacctccc aaccccgagg ggaccgagct caagcttcga acgcgtgcgg ccgcatcgat    2400
gccgtagtac ctttaagacc aatgacttac aaggcagctg tagatcttag ccactttta    2460 aaagaaaagg ggggactgga agggctaatt cactcccaaa gaagacaaga tccctgcagg    2520
cattcaaggc caggctggat gtggctctgg cagcctggg ctgctggttg atgaccctgc     2580
acatagcagg gggttggatc tggatgagca ctgtgctcct ttgcaaccca ggccgttcta    2640
tgattctgtc attctaaatc tctctttcag cctaaagctt ttttccccgta tccccccagg   2700 tgtctgcagg ctcaaagagc agcgagaagc gttcagagga aagcgatccc gtgccacctt    2760
ccccgtgccc gggctgtccc cgcacgctgc cggctcgggg atgcggggg agcgccggac     2820 cggagcggag ccccgggcgg ctcgctgctg cccctagcg ggggagggac gtaattacat     2880
ccctgggggc tttgggggg ggctgtcccc gtgagctccc cagatctgct ttttgcctgt     2940
actgggtctc tctggttaga ccagatctga gcctgggagc tctctggcta actagggaac    3000
ccactgctta agcctcaata aagcttcagc tgctcgagct agcagatctt tttccctctg    3060
ccaaaaatta tggggacatc atgaagcccc ttgagcatct gacttctggc taataaagga    3120
aatttatttt cattgcaata gtgtgttgga attttttgtg tctctcactc ggaaggacat    3180
atgggagggc aaatcattta aaacatcaga atgagtattt ggtttagagt ttggcaacat    3240
atgcccatat gctggctgcc atgaacaaag gttggctata aagaggtcat cagtatatga   3300
aacagccccc tgctgtccat tccttattcc atagaaaagc cttgacttga ggttagattt    3360
tttttatatt ttgttttgtg ttatttttt ctttaacatc cctaaaattt tccttacatg     3420
ttttactagc cagatttttc ctcctctcct gactactccc agtcatagct gtccctcttc    3480
tcttatggag atccctcgac ctgcagccca agcttggcgt aatcatggtc atagctgttt    3540
cctgtgtgaa attgttatcc gctcacaatt ccacacaaca tacgagccgg aagcataaag    3600
tgtaaagcct ggggtgccta atgagtgagc taactcacat taattgcgtt gcgctcactg    3660
cccgctttcc agtcgggaaa cctgtcgtgc cagcggatcc gcatctcaat tagtcagcaa    3720
ccatagtccc gcccctaact ccgcccatcc cgcccctaac tccgcccagt tccgcccatt    3780
ctccgcccca tggctgacta atttttttta tttatgcaga ggccgaggcc gcctcggcct    3840
ctgagctatt ccagaagtag tgaggaggct ttttggagg cctaggcttt tgcaaaaagc     3900
tgtcgactgc agaggcctgc atgcaagctt ggcgtaatca tggtcatagc tgtttcctgt    3960
gtgaaattgt tatccgctca caattccaca acatacga gccggaagca taaagtgtaa     4020
agcctggggt gcctaatgag tgagctaact cacattaatt gcgttgcgct cactgcccgc    4080
tttccagtcg ggaaacctgt cgtgccagct gcattaatga atcggccaac gcgcgggag     4140 aggcggtttg cgtattgggc gctcttccgc ttcctcgctc actgactcgc tgcgctcggt    4200
cgttcggctg cggcgagcgg tatcagctca ctcaaaggcg gtaatacggt tatccacaga    4260
atcaggggat aacgcaggaa agaacatgtg agcaaaaggc cagcaaaagg ccaggaaccg    4320
taaaaaggcc gcgttgctgg cgttttcca taggctccgc ccccctgacg agcatcacaa     4380
aaatcgacgc tcaagtcaga ggtggcgaaa cccgacagga ctataaagat accaggcgtt    4440
tccccctgga agctccctcg tgcgctctcc tgttccgacc ctgccgctta ccggatacct    4500
gtccgccttt ctcccttcgg gaagcgtggc gctttctcat agctcacgct gtaggtatct    4560
cagttcggtg taggtcgttc gctccaagct gggctgtgtg cacgaacccc cgttcagcc     4620 cgaccgctgc gccttatccg gtaactatcg tcttgagtcc aacccggtaa gacacgactt    4680
```

| | |
|---|---|
| atcgccactg gcagcagcca ctggtaacag gattagcaga gcgaggtatg taggcggtgc | 4740 |
| tacagagttc ttgaagtggt ggcctaacta cggctacact agaagaacag tatttggtat | 4800 |
| ctgcgctctg ctgaagccag ttaccttcgg aaaaagagtt ggtagctctt gatccggcaa | 4860 |
| acaaaccacc gctggtagcg gtggtttttt tgtttgcaag cagcagatta cgcgcagaaa | 4920 |
| aaaaggatct caagaagatc ctttgatctt ttctacgggg tctgacgctc agtggaacga | 4980 |
| aaactcacgt taagggattt tggtcatgag attatcaaaa aggatcttca cctagatcct | 5040 |
| tttaaattaa aaatgaagtt ttaaatcaat ctaaagtata tatgagtaaa cttggtctga | 5100 |
| cagttaccaa tgcttaatca gtgaggcacc tatctcagcg atctgtctat ttcgttcatc | 5160 |
| catagttgcc tgactccccg tcgtgtagat aactacgata cgggagggct taccatctgg | 5220 |
| ccccagtgct gcaatgatac cgcgagaccc acgctcaccg gctccagatt tatcagcaat | 5280 |
| aaaccagcca gccggaaggg ccgagcgcag aagtggtcct gcaactttat ccgcctccat | 5340 |
| ccagtctatt aattgttgcc gggaagctag agtaagtagt tcgccagtta atagtttgcg | 5400 |
| caacgttgtt gccattgcta caggcatcgt ggtgtcacgc tcgtcgtttg gtatggcttc | 5460 |
| attcagctcc ggttcccaac gatcaaggcg agttacatga tcccccatgt tgtgcaaaaa | 5520 |
| agcggttagc tccttcggtc ctccgatcgt tgtcagaagt aagttggccg cagtgttatc | 5580 |
| actcatggtt atggcagcac tgcataattc tcttactgtc atgccatccg taagatgctt | 5640 |
| ttctgtgact ggtgagtact caaccaagtc attctgagaa tagtgtatgc ggcgaccgag | 5700 |
| ttgctcttgc ccggcgtcaa tacgggataa taccgcgcca catagcagaa ctttaaaagt | 5760 |
| gctcatcatt ggaaaacgtt cttcggggcg aaaactctca aggatcttac cgctgttgag | 5820 |
| atccagttcg atgtaaccca ctcgtgcacc caactgatct tcagcatctt tactttcac | 5880 |
| cagcgtttct gggtgagcaa aaacaggaag gcaaaatgcc gcaaaaaagg gaataagggc | 5940 |
| gacacggaaa tgttgaatac tcatactctt cctttttcaa tattattgaa gcatttatca | 6000 |
| gggttattgt ctcatgagcg gatacatatt tgaatgtatt tagaaaaata acaaataggg | 6060 |
| gttccgcgc acatttcccc gaaaagtgcc acctgacgtc taagaaacca ttattatcat | 6120 |
| gacattaacc tataaaaata ggcgtatcac gaggcccttt cgtctcgcgc gtttcggtga | 6180 |
| tgacggtgaa aacctctgac acatgcagct cccggagacg gtcacagctt gtctgtaagc | 6240 |
| ggatgccggg agcagacaag cccgtcaggg cgcgtcagcg ggtgttggcg ggtgtcgggg | 6300 |
| ctggcttaac tatgcggcat cagagcagat tgtactgaga gtgcaccata tgcggtgtga | 6360 |
| aataccgcac agatgcgtaa ggagaaaata ccgcatcagg cgccattcgc cattcaggct | 6420 |
| gcgcaactgt tgggaagggc gatcggtgcg ggcctcttcg ctattacgcc agctggcgaa | 6480 |
| agggggatgt gctgcaaggc gattaagttg ggtaacgcca gggttttccc agtcacgacg | 6540 |
| ttgtaaaacg acggccagtg aattc | 6565 |

```
<210> SEQ ID NO 2
<211> LENGTH: 3901
<212> TYPE: DNA
<213> ORGANISM: Artificial Sequence
<220> FEATURE:
<223> OTHER INFORMATION: Synthetic: TL20C vector backbone

<400> SEQUENCE: 2
```

| | |
|---|---|
| ggccgcctcg gccaaacagc ccttgagttt accactccct atcagtgata gagaaaagtg | 60 |
| aaagtcgagt ttaccactcc ctatcagtga tagagaaaag tgaaagtcga gtttaccact | 120 |
| ccctatcagt gatagagaaa agtgaaagtc gagtttacca ctccctatca gtgatagaga | 180 |

```
aaagtgaaag tcgagtttac cagtccctat cagtgataga gaaaagtgaa agtcgagttt    240
accactccct atcagtgata gagaaaagtg aaagtcgagt ttaccactcc ctatcagtga    300
tagagaaaag tgaaagtcga gctcgccatg ggaggcgtgg cctgggcggg actggggagt    360
ggcgagccct cagatcctgc atataagcag ctgcttttg cctgtactgg gtctctctgg     420
ttagaccaga tctgagcctg ggagctctct ggctaactag ggaacccact gcttaagcct    480
caataaagct tgccttgagt gcttcaagta gtgtgtgccc gtctgttgtg tgactctggt    540
aactagagat ccctcagacc cttttagtca gtgtggaaaa tctctagcag tggcgcccga    600
acagggactt gaaagcgaaa gggaaaccag aggagctctc tcgacgcagg actcggcttg    660
ctgaagcgcg cacggcaaga ggcgaggggc ggcgactggt gagtacgcca aaattttga     720 ctagcggagg ctagaaggag agagatgggt gcgagagcgt cagtattaag cgggggagaa    780
ttagatcgcg atgggaaaaa attcggttaa ggccaggggg aaagaaaaaa tataaattaa    840
aacatatagt atgggcaagc agggagctag aacgattcgc agttaatact ggcctgttag    900
aaacatcaga aggctgtaga caaatactgg gacagctaca accatccctt cagacaggat    960
cagaagaact tagatcatta tataatacag tagcaaccct ctattgtgtg catcaaagga   1020
tagagataaa agacaccaag gaagctttag acaagataga ggaagagcaa acaaaagta    1080 agaaaaaagc acagcaagca gcaggatctt cagacctgga aattccctac aatccccaaa   1140
gtcaaggagt agtagaatct atgaataaag aattaaagaa aattatagga caggtaagag   1200
atcaggctga acatcttaag acagcagtac aaatggcagt attcatccac aattttaaaa   1260 gaaaagggg gattgggggg tacagtgcag gggaagaat agtagacata atagcaacag     1320
acatacaaac taagaattca caaaacaaa ttacaaaaat tcaaaatttt cgggtttatt    1380
acagggacag cagaaatcca ctttggaaag gaccagcaaa gctcctctgg aaaggtgaag   1440
gggcagtagt aatacaagat aatagtgaca taaagtagt gccaagaaga aaagcaaaga    1500
tcattaggga ttatggaaaa cagatggcag gtgatgattg tgtggcaagt agacaggatg   1560
aggattagaa catggaaaag tttagtaaaa caccataagg aggagatatg agggacaatt   1620
ggagaagtga attatataaa tataaagtag taaaaattga accattagga gtagcaccca   1680
ccaaggcaaa gagaagagtg gtgcagagag aaaaaagagc agtgggaata ggagctttgt   1740
tccttgggtt cttgggagca gcaggaagca ctatgggcgc agcgtcaatg acgctgacgg   1800
tacaggccag acaattattg tctggtatag tgcagcagca gaacaatttg ctgagggcta   1860
ttgaggcgca acagcatctg ttgcaactca gtctggggg catcaagcag ctccaggcaa    1920
gaatcctggc tgtggaaaga tacctaaagg atcaacagct cctggggatt tggggttgct   1980
ctggaaaact catttgcacc actgctgtgc cttggaatgc tagttggagt aataaatctc   2040
tggaacagat ttggaatcac acgacctgga tggagtggga cagagaaatt aacaattaca   2100
caagcttaat acactcctta attgaagaat cgcaaaacca gcaagaaaag aatgaacaag   2160
aattattgga attagataaa tgggcaagtt tgtggaattg gtttaacata caaaattggc   2220
tgtggtatat aaaattattc ataatgatag taggaggctt ggtaggttta agaatagttt   2280
ttgctgtact ttctatagtg aatagagtta ggcagggata ttcaccatta tcgtttcaga   2340
cccacctccc aaccccgagg ggaccgagct caagcttcga acgcgtgcgg ccgcatcgat   2400
gccgtagtac ctttaagacc aatgacttac aaggcagctg tagatcttag ccactttta    2460 aaagaaaagg ggggactgga agggctaatt cactcccaaa gaagacaaga tccctgcagg   2520
```

```
cattcaaggc caggctggat gtggctctgg gcagcctggg ctgctggttg atgaccctgc    2580
acatagcagg gggttggatc tggatgagca ctgtgctcct ttgcaaccca ggccgttcta    2640
tgattctgtc attctaaatc tctctttcag cctaaagctt tttccccgta tccccccagg    2700
tgtctgcagg ctcaaagagc agcgagaagc gttcagagga aagcgatccc gtgccacctt    2760
ccccgtgccc gggctgtccc cgcacgctgc cggctcgggg atgcgggggg agcgccggac    2820
cggagcggag ccccgggcgg ctcgctgctg cccctagcg ggggagggac gtaattacat     2880
ccctgggggc tttgggggg gctgtcccc gtgagctccc cagatctgct tttgcctgt       2940 actgggtctc tctggttaga ccagatctga gcctgggagc tctctggcta actagggaac    3000
ccactgctta agcctcaata aagcttcagc tgctcgagct agcagatctt tttccctctg    3060
ccaaaaatta tggggacatc atgaagcccc ttgagcatct gacttctggc taataaagga    3120
aatttatttt cattgcaata gtgtgttgga attttttgtg tctctcactc ggaaggacat    3180
atgggagggc aaatcattta aaacatcaga atgagtattt ggtttagagt ttggcaacat    3240
atgcccatat gctggctgcc atgaacaaag gttggctata aagaggtcat cagtatatga    3300
aacagccccc tgctgtccat tccttattcc atagaaaagc cttgacttga ggttagattt    3360
tttttatatt ttgttttgtg ttatttttt ctttaacatc cctaaaattt tccttacatg     3420
ttttactagc cagattttc ctcctctcct gactactccc agtcatagct gtccctcttc     3480
tcttatggag atccctcgac ctgcagccca agcttggcgt aatcatggtc atagctgttt    3540
cctgtgtgaa attgttatcc gctcacaatt ccacacaaca tacgagccgg aagcataaag    3600
tgtaaagcct ggggtgccta atgagtgagc taactcacat taattgcgtt gcgctcactg    3660
cccgctttcc agtcgggaaa cctgtcgtgc cagcggatcc gcatctcaat tagtcagcaa    3720
ccatagtccc gcccctaact ccgcccatcc cgccctaac tccgcccagt ccgcccatt     3780 ctccgcccca tggctgacta atttttttta tttatgcaga ggccgaggcc gcctcggcct    3840
ctgagctatt ccagaagtag tgaggaggct ttttggagg cctaggcttt tgcaaaaagc     3900
t                                                                    3901
```

<210> SEQ ID NO 3
<211> LENGTH: 343
<212> TYPE: DNA
<213> ORGANISM: Artificial Sequence
<220> FEATURE:
<223> OTHER INFORMATION: Synthetic: nucleotide sequence encoding the
      packing signal

<400> SEQUENCE: 3

```
agtattaagc gggggagaat tagatcgcga tgggaaaaaa ttcggttaag gccaggggga    60
aagaaaaaat ataattaaa acatatagta tgggcaagca gggagctaga acgattcgca     120
gttaatactg gcctgttaga aacatcagaa ggctgtagac aaatactggg acagctacaa    180
ccatcccttc agacaggatc agaagaactt agatcattat ataatacagt agcaaccctc    240
tattgtgtgc atcaaaggat agagataaaa gacaccaagg aagctttaga caagatagag    300
gaagagcaaa acaaaagtaa gaaaaaagca cagcaagcag cag                      343
```

<210> SEQ ID NO 4
<211> LENGTH: 477
<212> TYPE: DNA
<213> ORGANISM: Artificial Sequence
<220> FEATURE:
<223> OTHER INFORMATION: Synthetic: Central polypurine tract (cppt)

<400> SEQUENCE: 4

```
aattccctac aatccccaaa gtcaaggagt agtagaatct atgaataaag aattaaagaa    60
aattatagga caggtaagag atcaggctga acatcttaag acagcagtac aaatggcagt   120
attcatccac aattttaaaa gaaaaggggg gattgggggg tacagtgcag gggaaagaat   180
agtagacata atagcaacag acatacaaac taaagaatta caaaaacaaa ttacaaaaat   240
tcaaaatttt cgggtttatt acagggacag cagaaatcca ctttggaaag gaccagcaaa   300
gctcctctgg aaaggtgaag gggcagtagt aatacaagat aatagtgaca taaaagtagt   360
gccaagaaga aaagcaaaga tcattaggga ttatggaaaa cagatggcag gtgatgattg   420
tgtggcaagt agacaggatg aggattagaa catggaaaag tttagtaaaa caccata      477
```

<210> SEQ ID NO 5
<211> LENGTH: 769
<212> TYPE: DNA
<213> ORGANISM: Artificial Sequence
<220> FEATURE:
<223> OTHER INFORMATION: Synthetic: nucleotide sequence encoding the rev response element

<400> SEQUENCE: 5

```
aggaggagat atgagggaca attggagaag tgaattatat aaatataaag tagtaaaaat    60
tgaaccatta ggagtagcac ccaccaaggc aaagagaaga gtggtgcaga gagaaaaaag   120
agcagtggga ataggagctt tgttccttgg gttcttggga gcagcaggaa gcactatggg   180
cgcagcgtca atgacgctga cggtacaggc cagacaatta ttgtctggta tagtgcagca   240
gcagaacaat ttgctgaggg ctattgaggc gcaacagcat ctgttgcaac tcacagtctg   300
gggcatcaag cagctccagg caagaatcct ggctgtggaa agatacctaa aggatcaaca   360
gctcctgggg atttggggtt gctctggaaa actcatttgc accactgctg tgccttggaa   420
tgctagttgg agtaataaat ctctggaaca gatttggaat cacacgacct ggatggagtg   480
ggacagagaa attaacaatt acacaagctt aatacactcc ttaattgaag aatcgcaaaa   540
ccagcaagaa aagaatgaac aagaattatt ggaattagat aaatgggcaa gtttgtggaa   600
ttggttttaac ataacaaatt ggctgtggta tataaaatta ttcataatga tagtaggagg   660
cttggtaggt ttaagaatag ttttttgctgt actttctata gtgaatagag ttaggcaggg   720
atattcacca ttatcgtttc agacccacct cccaaccccg aggggaccg              769
```

<210> SEQ ID NO 6
<211> LENGTH: 181
<212> TYPE: DNA
<213> ORGANISM: Artificial Sequence
<220> FEATURE:
<223> OTHER INFORMATION: Synthetic: nucleotide sequence encoding the self-inactivating long terminal repeat

<400> SEQUENCE: 6

```
gggtctctct ggttagacca gatctgagcc tgggagctct ctggctaact agggaaccca    60
ctgcttaagc ctcaataaag cttgccttga gtgcttcaag tagtgtgtgc ccgtctgttg   120
tgtgactctg gtaactagag atccctcaga ccctttagt cagtgtggaa aatctctagc   180
a                                                                  181
```

<210> SEQ ID NO 7
<211> LENGTH: 25
<212> TYPE: DNA
<213> ORGANISM: Artificial Sequence
<220> FEATURE:
<223> OTHER INFORMATION: Synthetic: nucleotide sequence encoding the
      multiple cloning site

<400> SEQUENCE: 7
ttcgaacgcg tgcggccgca tcgat                                            25

<210> SEQ ID NO 8
<211> LENGTH: 1978
<212> TYPE: DNA
<213> ORGANISM: Artificial Sequence
<220> FEATURE:
<223> OTHER INFORMATION: Synthetic: LVSH5/C46

<400> SEQUENCE: 8
gaacgctgac gtcatcaacc cgctccaagg aatcgcgggc ccagtgtcac taggcgggaa      60
cacccagcgc gcgtgcgccc tggcaggaag atggctgtga gggacagggg agtggcgccc    120
tgcaatattt gcatgtcgct atgtgttctg ggaaatcacc ataaacgtga atgtctttg     180 gatttgggaa tcttataagt tctgtatgag accacggatc cccgagcaag ctcagtttac    240
accttgtccg acggtgtaaa ctgagcttgc tcttttgag acgagtcctc gagccataaa     300
gatggttaat taacccaccc aagatctggc ctccgcgccg ggttttggcg cctcccgcgg    360
gcgcccccct cctcacggcg agcgctgcca cgtcagacga agggcgcagc gagcgtcctg    420
atccttccgc ccgacgctc aggacagcgg cccgctgctc ataagactcg gccttagaac     480
cccagtatca gcagaaggac attttaggac gggacttggg tgactctagg cactggtttt   540
tctttccaga gagcggaaca ggcgaggaaa agtagtccct tctcggcgat ctgcggagg     600 gatctccgtg gggcggtgaa cgccgatgat tatataagga cgcgccgggt gtggcacagc    660
tagttccgtc gcagccggga tttggtcgc ggttcttgtt tgtggatcgc tgtgatcgtc     720
acttggtgag tagcgggctg ctgggctggc cggggctttc gtggccgccg gccgctcgg    780 tgggacggaa gcgtgtggag agaccgccaa gggctagt ctgggtccgc gagcaaggtt      840
gccctgaact gggggttggg gggagcgcag caaaatggcg gctgttcccg agtcttgaat    900
ggaagacgct tgtgaggcgg gctgtgaggt cgttgaaaca aggtgggggg catggtgggc   960
ggcaagaacc caaggtcttg aggccttcgc taatgcggga aagctcttat tcgggtgaga   1020
tgggctgggg caccatctgg ggaccctgac gtgaagtttg tcactgactg gagaactcgg   1080
tttgtcgtct gttgcggggg cggcagttat ggcggtgccg ttgggcagtg caccgtacc    1140 tttgggagcg cgcgcccctcg tcgtgtcgtg acgtcacccg ttctgttggc ttataatgca  1200
gggtggggcc acctgccggt aggtgtgcgg taggcttttc tccgtcgcag gacgcagggt   1260
tcgggcctag ggtaggctct cctgaatcga caggcgccgg acctctggtg aggggaggga   1320
taagtgaggc gtcagtttct ttggtcggtt ttatgtacct atcttcttaa gtagctgaag   1380
ctccggtttt gaactatgcg ctcggggttg gcgagtgtgt tttgtgaagt ttttaggca    1440 ccttttgaaa tgtaatcatt tgggtcaata tgtaattttc agtgttagac tagtaaattg   1500
tccgctaaat tctggccgtt tttggctttt ttgttagacg aagcttggta ccgagctcgg   1560
atccgccacc atgggagcag agcaaccgg aagggcaatg gacggaccaa gattgttact   1620
tctgctcctg ctaggcgtga gcctgggagg agcaaggagc tggatggagt gggacaggga   1680
gatcaacaac tacaccagcc tgatccacag cctgatcgag gagagccaga accagcagga   1740
gaagaacgag caggagctgc tggagctgga caagtgggcc agcctgtgga actggttccg   1800
gagcgagcgg aagtgctgcg tggagtgccc accatgccca gcaccaccag tggcaggacc   1860

```
cctgatcgca ctggtgacca gcggagccct gctggccgtg ctgggcatca caggctactt    1920
cctgatgaac aggaggagct ggagcccaac cggagagcgg ctggagctgg agccatga     1978

<210> SEQ ID NO 9
<211> LENGTH: 1113
<212> TYPE: DNA
<213> ORGANISM: Artificial Sequence
<220> FEATURE:
<223> OTHER INFORMATION: Synthetic: PGK-BLE SEQUENCE

<400> SEQUENCE: 9
ccagcctttg gaattcctgc aggatgggat tctaccgggt aggggaggcg ctttcccaa      60 ggcagtctgg agcatgcgct ttagcagccc cgctgggcac ttggcgctac acaagtggcc    120
tctggcctcg cacacattcc acatccaccg gtaggcgcca accggctccg ttctttggtg    180
gccccttcgc gccaccttct actcctcccc tagtcaggaa gttcccccc gccccgcagc     240 tcgcgtcgtg caggacgtga caaatggaag tagcacgtct cactagtctc gtgcagatgg    300
acagcaccgc tgagcaatgg aagcgggtag gcctttgggg cagcggccaa tagcagcttt    360
gctccttcgc tttctgggct caggggcggg cggggcgccc gaaggtcctc cggaggcccg    420
gcattctgca cgcttcaaaa gcgcacgtct gccgcgctgt tctcctcttc ctcatctccg    480
ggcctttcga cctggatcct gcagcacgtg ttgacaatta atcatcggca tagtatatcg    540
gcatagtata atacgactca ctataggagg gccaccatgg ccaagttgac cagtgccgtt    600
ccggtgctca ccgcgcgcga cgtcgccgga gcggtcgagt tctggaccga ccggctcggg    660
ttctcccggg acttcgtgga ggacgacttc gccggtgtgg tccgggacga cgtgaccctg    720
ttcatcagcg cggtccagga ccaggtggtg ccggacaaca ccctggcctg ggtgtgggtg    780
cgcggcctgg acgagctgta cgccgagtgg tcggaggtcg tgtccacgaa cttccgggac    840
gcctccgggc cggccatgac cgagatcggc gagcagccgt gggggcggga gttcgccctg    900
cgcgacccgg ccggcaactg cgtgcacttc gtggccgagg agcaggactg atgctttatt    960
tgtgaaattt gtgatgctat tgctttattt gtaaccatta taagctgcaa taaacaagtt   1020
aacaacaaca attgcattca ttttatgttt caggttcagg gggaggtgtg ggaggttttt   1080
taaactagtg agtcgtatta cccagccttt ggg                                1113

<210> SEQ ID NO 10
<211> LENGTH: 288
<212> TYPE: DNA
<213> ORGANISM: Artificial Sequence
<220> FEATURE:
<223> OTHER INFORMATION: Synthetic: (7tetO): doxycycline repressible
      promoter

<400> SEQUENCE: 10
tttaccactc cctatcagtg atagagaaaa gtgaaagtcg agtttaccac tccctatcag     60
tgatagagaa aagtgaaagt cgagtttacc actccctatc agtgatagag aaaagtgaaa   120
gtcgagttta ccactcccta tcagtgatag agaaaagtga agtcgagtt accagtccc     180 tatcagtgat agagaaaagt gaaagtcgag tttaccactc cctatcagtg atagagaaaa   240
gtgaaagtcg agtttaccac tccctatcag tgatagagaa aagtgaaa                288

<210> SEQ ID NO 11
<211> LENGTH: 98
<212> TYPE: DNA
<213> ORGANISM: Artificial Sequence
```

<220> FEATURE:
<223> OTHER INFORMATION: Synthetic: HIV LTR R5 region

<400> SEQUENCE: 11

```
gggtctctct ggttagacca gatctgagcc tgggagctct ctggctaact agggaaccca    60
ctgcttaagc ctcaataaag cttgccttga gtgcttca                           98
```

<210> SEQ ID NO 12
<211> LENGTH: 83
<212> TYPE: DNA
<213> ORGANISM: Artificial Sequence
<220> FEATURE:
<223> OTHER INFORMATION: Synthetic: HIV LTR U5 region

<400> SEQUENCE: 12

```
agtagtgtgt gcccgtctgt tgtgtgactc tggtaactag agatccctca gacccttta    60
gtcagtgtgg aaaatctcta gca                                           83
```

<210> SEQ ID NO 13
<211> LENGTH: 412
<212> TYPE: DNA
<213> ORGANISM: Artificial Sequence
<220> FEATURE:
<223> OTHER INFORMATION: Synthetic: chicken HS4 400 bp chromatin
      insulator

<400> SEQUENCE: 13

```
atccctgcag gcattcaagg ccaggctgga tgtggctctg ggcagcctgg gctgctggtt   60
gatgaccctg cacatagcag gggggttggat ctggatgagc actgtgctcc tttgcaaccc  120
aggccgttct atgattctgt cattctaaat ctctctttca gcctaaagct ttttccccgt   180
atcccccag gtgtctgcag gctcaaagag cagcgagaag cgttcagagg aaagcgatcc    240
cgtgccacct tccccgtgcc cgggctgtcc ccgcacgctg ccggctcggg gatgcgggggg   300
gagcgccgga ccggagcgga gccccgggcg gctcgctgct gcccccctagc ggggagggga  360
cgtaattaca tccctggggg ctttgggggg gggctgtccc cgtgagctcc cc          412
```

<210> SEQ ID NO 14
<211> LENGTH: 449
<212> TYPE: DNA
<213> ORGANISM: Artificial Sequence
<220> FEATURE:
<223> OTHER INFORMATION: Synthetic: rabbit beta-globin polyadenylation
      signal

<400> SEQUENCE: 14

```
gatctttttc cctctgccaa aaattatggg gacatcatga agccccttga gcatctgact   60
tctggctaat aaaggaaatt tatttcatt gcaatagtgt gttggaattt tttgtgtctc   120
tcactcggaa ggacatatgg gagggcaaat catttaaaac atcagaatga gtatttggtt   180
tagagttttgg caacatatgc ccatatgctg gctgccatga acaaaggttg gctataaaga   240
ggtcatcagt atatgaaaca gccccctgct gtccattcct tattccatag aaaagccttg   300
acttgaggtt agattttttt tatatttttgt tttgtgttat ttttttcttt aacatcccta   360
aaattttcct tacatgtttt actagccaga ttttcctcc tctcctgact actcccagtc   420
atagctgtcc ctcttctctt atggagatc                                    449
```

<210> SEQ ID NO 15
<211> LENGTH: 2664
<212> TYPE: DNA

<213> ORGANISM: Artificial Sequence
<220> FEATURE:
<223> OTHER INFORMATION: Synthetic: pUC57 Plasmid portion

<400> SEQUENCE: 15

```
gtcgactgca gaggcctgca tgcaagcttg gcgtaatcat ggtcatagct gtttcctgtg      60
tgaaattgtt atccgctcac aattccacac aacatacgag ccggaagcat aaagtgtaaa     120
gcctggggtg cctaatgagt gagctaactc acattaattg cgttgcgctc actgcccgct     180
ttccagtcgg gaaacctgtc gtgccagctg cattaatgaa tcggccaacg cgcggggaga     240
ggcggtttgc gtattgggcg ctcttccgct tcctcgctca ctgactcgct gcgctcggtc     300
gttcggctgc ggcgagcggt atcagctcac tcaaaggcgg taatacggtt atccacagaa     360
tcaggggata acgcaggaaa gaacatgtga gcaaaaggcc agcaaaaggc caggaaccgt     420
aaaaaggccg cgttgctggc gtttttccat aggctccgcc cccctgacga gcatcacaaa     480
aatcgacgct caagtcagag gtggcgaaac ccgacaggac tataaagata ccaggcgttt     540
ccccctggaa gctccctcgt gcgctctcct gttccgaccc tgccgcttac cggatacctg     600
tccgcctttc tcccttcggg aagcgtggcg ctttctcata gctcacgctg taggtatctc     660
agttcggtgt aggtcgttcg ctccaagctg ggctgtgtgc acgaaccccc cgttcagccc     720
gaccgctgcg ccttatccgg taactatcgt cttgagtcca acccggtaag acacgactta     780
tcgccactgg cagcagccac tggtaacagg attagcagag cgaggtatgt aggcggtgct     840
acagagttct tgaagtggtg cctaactacg gctacacta gaagaacagt atttggtatc     900
tgcgctctgc tgaagccagt taccttcgga aaaagagttg gtagctcttg atccggcaaa     960
caaaccaccg ctggtagcgg tggttttttt gtttgcaagc agcagattac gcgcagaaaa    1020
aaaggatctc aagaagatcc tttgatcttt tctacggggt ctgacgctca gtggaacgaa    1080
aactcacgtt aagggatttt ggtcatgaga ttatcaaaaa ggatcttcac ctagatcctt    1140
ttaaattaaa aatgaagttt taaatcaatc taaagtatat atgagtaaac ttggtctgac    1200
agttaccaat gcttaatcag tgaggcacct atctcagcga tctgtctatt tcgttcatcc    1260
atagttgcct gactccccgt cgtgtagata actacgatac gggagggctt accatctggc    1320
cccagtgctg caatgatacc gcgagaccca cgctcaccgg ctccagattt atcagcaata    1380
aaccagccag ccggaagggc cgagcgcaga agtggtcctg caactttatc cgcctccatc    1440
cagtctatta attgttgccg ggaagctaga gtaagtagtt cgccagttaa tagtttgcgc    1500
aacgttgttg ccattgctac aggcatcgtg gtgtcacgct cgtcgtttgg tatggcttca    1560
ttcagctccg gttcccaacg atcaaggcga gttacatgat cccccatgtt gtgcaaaaaa    1620
gcggttagct ccttcggtcc tccgatcgtt gtcagaagta agttggccgc agtgttatca    1680
ctcatggtta tggcagcact gcataattct cttactgtca tgccatccgt aagatgcttt    1740
tctgtgactg gtgagtactc aaccaagtca ttctgagaat agtgtatgcg gcgaccgagt    1800
tgctcttgcc cggcgtcaat acgggataat accgcgccac atagcagaac tttaaaagtg    1860
ctcatcattg gaaaacgttc ttcggggcga aaactctcaa ggatcttacc gctgttgaga    1920
tccagttcga tgtaacccac tcgtgcaccc aactgatctt cagcatcttt tactttcacc    1980
agcgtttctg ggtgagcaaa aacaggaagg caaaatgccg caaaaaaggg aataagggcg    2040
acacggaaat gttgaatact catactcttc ctttttcaat attattgaag catttatcag    2100
ggttattgtc tcatgagcgg atacatattt gaatgtattt agaaaaataa acaaataggg    2160
gttccgcgca catttccccg aaaagtgcca cctgacgtct aagaaaccat tattatcatg    2220
```

```
acattaacct ataaaaatag gcgtatcacg aggccctttc gtctcgcgcg tttcggtgat    2280
gacggtgaaa acctctgaca catgcagctc ccggagacgg tcacagcttg tctgtaagcg    2340
gatgccggga gcagacaagc ccgtcagggc gcgtcagcgg gtgttggcgg gtgtcggggc    2400
tggcttaact atgcggcatc agagcagatt gtactgagag tgcaccatat gcggtgtgaa    2460
ataccgcaca gatgcgtaag gagaaaatac cgcatcaggc gccattcgcc attcaggctg    2520
cgcaactgtt gggaagggcg atcggtgcgg gcctcttcgc tattacgcca gctggcgaaa    2580
gggggatgtg ctgcaaggcg attaagttgg gtaacgccag ggttttccca gtcacgacgt    2640
tgtaaaacga cggccagtga attc                                          2664
```

BIO-PRODUCTION OF LENTIVIRAL VECTORS

CROSS-REFERENCE TO RELATED APPLICATIONS

This application is a continuation of International Application No. PCT/US2016/031959, filed May 12, 2016; which application claims the benefit of the filing date of U.S. Provisional Patent Application No. 62/161,133, filed May 13, 2015; and the benefit of the filing date of U.S. Provisional Patent Application No. 62/161,152, filed May 13, 2015, the disclosures of which are hereby incorporated by reference herein in their entireties.

FIELD OF DISCLOSURE

This disclosure generally relates to the fields of molecular biology and virology. In particular, the disclosure relates to the bio-production of lentiviral vectors and lentiviral transfer plasmids.

STATEMENT OF INDUSTRIAL APPLICABILITY

The present disclosure has industrial applicability in the field of gene therapeutics and bio-manufacturing.

BACKGROUND OF THE DISCLOSURE

HIV-1 is the causative agent of Acquired Immunodeficiency Syndrome (AIDS) with of the order of 30 million individuals infected world-wide. HIV causes the immune system to fail and increases the probability of death due to opportunistic infections. HIV infection is a major global health problem as evidenced by its designation as a pandemic by the World Health Organization. Most people who are infected with HIV, particularly in the developing world, eventually develop AIDS, which claims the lives of more than one million people every year.

HIV-1 belongs to the retroviridae family of viruses, and is an enveloped virus whose genome consists of two single stranded RNA molecules (ssRNA). The primary target of HIV-1 is CD4+ expressing cells, such as CD4+ T cells. A glycoprotein of the HIV-1 virus interacts with the CD4 molecule of target cells and with chemokine co-receptors, CCR5 or CXCR4 on the surface of target cells. Following fusion and entry into the target cell, the nucleocapsid containing the viral genome dissociates, releasing the contents of the virus, including the ssRNA, into the cytoplasm. A reverse transcriptase (RT) enzyme of HIV-1 synthesizes viral double stranded DNA (dsDNA) from the ssRNA genome. Following synthesis of the double stranded HIV-1 DNA molecule, the HIV-1 DNA is integrated into the host genome.

The integrated HIV-1 DNA is flanked by identical 5' and 3' long terminal repeat sequences (LTR) from which HIV-1 can initiate transcription of the integrated HIV-1 genome. Transcription of the viral DNA requires transcription factors, such as NF-kB, which are upregulated in activated T cells. As a consequence, viral transcription is most active in the T cell following activation of the T cell, such as during infection. Viral RNA resulting from transcription of the integrated HIV-1 genome is subsequently translated and packaged into virus particles which then exit the cell to become infectious virus.

Therapy for HIV-1 infection includes combination anti-retroviral therapy (cART). cART, which includes combinations of nucleoside analogue reverse transcriptase inhibitors, protease inhibitors, non-nucleoside reverse transcriptase inhibitors, integrase and fusion inhibitors, slows HIV progression. This, in turn, dramatically decreases the morbidity and mortality rate from HIV/AIDS in regions of the world where the therapy is available. However, cART does not cure or completely eliminate all the symptoms of HIV/AIDS. Also, cART therapy can be compromised by drug resistant mutations, and has a range of side effects which can be serious and which appear to be cumulative. Further, interruption of cART therapy almost invariably leads to the re-emergence of detectable viral replication and the progression to AIDS and has been shown to be associated with an increased incidence of all causes of mortality and serious non AIDS events. For these reasons, as well as the high cost of cART and need for strict adherence, such therapy can be relatively ineffective for a large number of patients.

HIV-based lentiviral vectors are rapidly becoming the retrovirus vector system of choice for research and clinical gene transfer applications. The enhanced ability of lentiviral vectors to transduce both quiescent stem cells and non-dividing terminally differentiated cells has led to the development of a wide range of therapeutic gene delivery vectors, as well as promising research tools, such as short hairpin RNA (shRNA) gene knockdown libraries and vectors for induction of pluripotency in terminally differentiated cells. Early gamma-retroviral clinical gene therapy vectors restored immune function in patients with X-linked severe combined immunodeficiency (SCID-X1), but they were subsequently found to cause proliferative disorders via transactivation of proto-oncogenes. Newer lentiviral vector designs may significantly reduce that risk, and they await clinical testing for final validation of their predicted safety. The field remains in flux and the outcomes of the clinical testing are unpredictable.

Producing SIN—lentiviral vectors at scales to support clinical trials is an important challenge within the field. While gamma-retroviral vectors can be produced by either transient transfection or the generation of stable producer cell lines, lentiviruses require the expression of multiple cytotoxic accessory genes, which makes the generation of producer cells more complicated (Greene et al., Transduction of Human CD34+ Repopulating Cells with a Self—Inactivating Lentiviral Vector for SCID-X1 Produced at Clinical Scale by a Stable Cell Line, HG™, 23, 297-308 (October 2012), which is hereby incorporated by reference in its entirety). Transient transfection is instead the current technology for pilot production of LV, which is impractical for very large-scale applications under a safety, cost, and reproducibility standpoint. In fact, this technology is expensive, is difficult to standardize and scale-up, and suffers from batch-to-batch variability and low reverse transcriptase fidelity (Stornaiuolo et al., RD2-MolPack-Chim3, a Packaging Cell Line for Stable Production of Lentiviral Vectors for Anti-HIV Gene Therapy, HGTM, 24:228-240 (August 2013), which is hereby incorporated by reference in its entirety).

SUMMARY OF THE DISCLOSURE

In one aspect of the present disclosure is a plasmid comprising a nucleotide sequence having at least 90% identity to that of SEQ ID NO: 1. In some embodiments, the nucleotide sequence has at least 95% identity to that of sequence of SEQ ID NO: 1. In some embodiments, a lentiviral vector is derived from the plasmid. In some embodiments, the derived lentiviral vector comprises one or more additional sequences encoding a short hairpin RNA for down-regulation of an HIV-1 co-receptor and/or an HIV-1 fusion inhibitor. In some embodiments, the lentiviral vector derived therefrom is LVsh5/C46 (as defined herein).

In another aspect of the present disclosure is a plasmid comprising the nucleotide sequence of SEQ ID NO: 1. In some embodiments, a lentiviral vector is derived from the plasmid. In some embodiments, the derived lentiviral vector comprises one or more additional sequences encoding a short hairpin RNA for down-regulation of an HIV-1 co-receptor (e.g. CCR5) and/or an HIV-1 fusion inhibitor (e.g. C46). Information regarding CCR5 and C46, including their nucleotide sequences, is set forth further in US Patent Publication No. US2012/0201794, the disclosure of which is incorporated by reference herein in its entirety.

In another aspect of the present disclosure is a plasmid comprising a nucleotide sequence having at least 80% identify to that of SEQ NO: 2. In some embodiments, the plasmid comprises a nucleotide sequence having at least 90% identify to that of SEQ NO: 2. In some embodiments, the plasmid comprises a nucleotide sequence having at least 95% identify to that of SEQ NO: 2. In some embodiments, the plasmid comprises a nucleotide sequence having at least 97% identify to that of SEQ NO: 2. In some embodiments, the plasmid comprises the nucleotide sequence of SEQ NO: 2. In some embodiments, a lentiviral vector is derived from the plasmid. In some embodiments, the derived lentiviral vector comprises one or more additional sequences encoding a short hairpin RNA for down-regulation of an HIV-1 co-receptor (e.g. CCR5) and/or an HIV-1 fusion inhibitor (e.g. C46).

In another aspect of the present disclosure is a plasmid having a sequence that differs by not more than 500 nucleotides from the sequence set forth in SEQ ID NO: 1 (e.g. non-consecutive or consecutive). In another aspect of the present disclosure is a plasmid having a sequence that differs by not more than 250 nucleotides from the sequence set forth in SEQ ID NO: 1 (e.g. non-consecutive or consecutive). In another aspect of the present disclosure is a plasmid having a sequence that differs by not more than 150 nucleotides from the sequence set forth in SEQ ID NO: 1 (e.g. non-consecutive or consecutive). In another aspect of the present disclosure is a plasmid having a sequence that differs by not more than 100 nucleotides from the sequence set forth in SEQ ID NO: 1 (e.g. non-consecutive or consecutive). In some embodiments, the sequence differs by not more than 50 nucleotides from the sequence set forth in SEQ ID NO: 1 (e.g. non-consecutive or consecutive).

In another aspect of the present disclosure is a plasmid comprising between about 6500 nucleotides and about 6750 nucleotides, and wherein the plasmid comprises a sequence or fragment thereof having at least 90% identity to that of SEQ ID NO: 2. In some embodiments, the plasmid comprises between about 6600 nucleotides and about 6700 nucleotides. In some embodiments, the plasmid comprises about 6611 nucleotides.

In another aspect of the present disclosure is a plasmid as set forth in FIG. 11 as pUC57-TL20c. In some embodiments, a lentiviral vector is derived from the plasmid. In some embodiments, the derived lentiviral vector comprises one or more additional sequences encoding a short hairpin RNA for down-regulation of an HIV-1 co-receptor and/or an HIV-1 fusion inhibitor.

In another aspect of the present disclosure is a plasmid comprising a multiple cloning site consisting essentially of the BstBI, MluI, NotI, and ClaI restriction endonuclease sites. In some embodiments, the plasmid further comprises a nucleotide sequence encoding a packaging signal; a nucleotide sequence encoding a central polypurine tract; a nucleotide sequence encoding a Rev response element; and a nucleotide sequence encoding a self-inactivating long terminal repeat. In other embodiments, the plasmid comprises a multiple cloning site consisting of the BstBI, MluI, NotI, and ClaI restriction endonuclease sites. In some embodiments, a lentiviral vector is derived from the plasmid. In some embodiments, the derived lentiviral vector comprises one or more additional sequences encoding a short hairpin RNA for down-regulation of an HIV-1 co-receptor and/or an HIV-1 fusion inhibitor.

In another aspect of the present disclosure is a plasmid comprising (a) a nucleotide sequence encoding a packaging signal; (b) a nucleotide sequence encoding a central polypurine tract (cPPT); (c) a nucleotide sequence encoding a Rev response element; (d) a nucleotide sequence encoding a self-inactivating long terminal repeat; and (e) a nucleotide sequence encoding a multiple cloning site having restriction sites for the enzymes BstBI, Mlu I, Not I, and Cla I. In some embodiments, the nucleotide sequence encoding the packing signal comprises the sequence of SEQ ID NO: 3. In some embodiments, the nucleotide sequence encoding the central polypurine tract (cPPT) comprises the sequence of SEQ ID NO: 4. In some embodiments, the nucleotide sequence encoding the Rev response element comprises the sequence of SEQ ID NO: 5. In some embodiments, the nucleotide sequence encoding the self-inactivating long terminal repeat comprises the sequence of SEQ ID NO: 6. In some embodiments, the nucleotide sequence encoding the multiple cloning site comprises the sequence of SEQ ID NO: 7.

In another aspect of the present disclosure is a plasmid comprising (a) a packaging sequence, the packaging sequence present from about nucleotide 762 to about nucleotide 1104 of a nucleotide sequence of the plasmid; (b) a central polypurine tract, the central polypurine tract present from about nucleotide 1121 to about nucleotide 1597 of the plasmid nucleotide sequence; (c) a Rev response element, the Rev response element present from about nucleotide 1598 to about nucleotide 2366 of the plasmid nucleotide sequence; (d) a self-inactivating long terminal repeat, the self-inactivating long terminal repeat present from about nucleotide 409 to about nucleotide 589 of the plasmid nucleotide sequence; and (e) a multiple cloning site, the multiple cloning site present from about nucleotide 2376 to about nucleotide 2400 of the plasmid nucleotide sequence. In some embodiments, the plasmid nucleotide sequence comprises a sequence having at least 90% identity to that of SEQ ID NO: 1. In some embodiments, a nucleotide sequence encoding the packing signal comprises the sequence of SEQ ID NO: 3. In some embodiments, nucleotide sequence encoding the central polypurine tract (cPPT) comprises the sequence of SEQ ID NO: 4. In some embodiments, a nucleotide sequence encoding the Rev response element comprises the sequence of SEQ ID NO: 5. In some embodiments, a nucleotide sequence encoding the self-inactivating long terminal repeat comprises the sequence of SEQ ID NO: 6. In some embodiments, a nucleotide sequence encoding the multiple cloning site comprises the sequence of SEQ ID NO: 7.

In another aspect of the present disclosure is a plasmid comprising a multiple cloning site comprising the BstBI, MluI, NotI, and ClaI restriction endonuclease sites, and wherein the plasmid comprises a nucleotide sequence having at least 80% identify to that of SEQ ID NO: 1. In some embodiments, a lentiviral vector is derived from the plasmid. In some embodiments, the derived lentiviral vector comprises one or more additional sequences encoding a short hairpin RNA for down-regulation of an HIV-1 co-receptor and/or an HIV-1 fusion inhibitor.

In another aspect of the present disclosure is a plasmid comprising a nucleotide sequence encoding a vector backbone having at least 95% identity to that of SEQ ID NO: 2, and wherein the vector backbone is flanked by at least two additional restriction endonuclease sites, the at least two additional restriction endonuclease sites independently are selected from the group consisting of sfiI and Bsu36I. In some embodiments, a lentiviral vector is derived from the plasmid. In some embodiments, the derived lentiviral vector comprises one or more additional sequences encoding a short hairpin RNA for down-regulation of an HIV-1 co-receptor and/or an HIV-1 fusion inhibitor.

In another aspect of the present disclosure is plasmid comprising a nucleotide sequence encoding a vector backbone having at least 90% identity to that of SEQ ID NO: 2, the vector backbone comprising a multiple cloning site having BstBI, MluI, NotI, and ClaI restriction endonuclease sites, wherein the plasmid further comprises a tetracycline repressible promoter upstream of the vector backbone. In yet another aspect of the present disclosure is plasmid comprising a nucleotide sequence encoding a vector backbone having at least 85% identity to that of SEQ ID NO: 2, the vector backbone consisting of a multiple cloning site having BstBI, MluI, NotI, and ClaI restriction endonuclease sites, In another aspect of the present disclosure is a cell comprising a plasmid or a lentiviral vector derived therefrom as described herein. In some embodiments, the cell is a hematopoietic progenitor/stem cell, a monocyte, a macrophage, a peripheral blood mononuclear cell, a CD4+ T lymphocyte, a CD8+ T lymphocyte, or a dendritic cell. In another aspect of the present invention is a kit comprising hematopoietic progenitor/stem cells in a first container and the plasmid of FIG. 11 or a lentiviral vector derived therefrom.

In another aspect of the present disclosure is a method of producing a stable producer cell line comprising: (a) synthesizing a lentiviral vector by cloning one or more genes into a plasmid as described herein, e.g. pUC57-TL20c; (b) generating DNA fragments from the synthesized lentiviral vector; (c) forming a concatemeric array from the generated DNA fragments of the synthesized lentiviral vector and from DNA fragments from an antibiotic resistance cassette plasmid; (d) transfecting a GPR, GPRG, GPRT, GPRGT or GPRT-G packing cell line or a derivative thereof with the formed concatemeric array; and (e) isolating one or more stable producer cell line clones. In some embodiments, the method further comprises inducing the stable producer cell line to produce the lentiviral vector.

In another aspect of the present disclosure is a method of producing a stable producer cell line comprising: (a) synthesizing a lentiviral vector which encodes a short hairpin RNA for down-regulation of an HIV-1 co-receptor and which encodes an HIV-1 fusion inhibitor, the lentiviral vector synthesized by cloning cDNA encoding both the short hairpin RNA and the fusion inhibitor into a plasmid as described herein; (b) generating DNA fragments from the synthesized lentiviral vector; (c) forming a concatemeric array from the generated DNA fragments from the synthesized lentiviral vector and from DNA fragments from an antibiotic resistance cassette plasmid; (d transfecting a GPR, GPRG, GPRT, GPRGT or GPRT-G packing cell line or a derivative thereof with the formed concatemeric array; and (e) isolating one or more stable producer cell line clones. In some embodiments, the method further comprises inducing the stable producer cell line to produce the lentiviral vector which encodes a short hairpin RNA for down-regulation of an HIV-1 co-receptor and which encodes an HIV-1 fusion inhibitor (LVsh5/C46).

In another aspect of the present disclosure is a method of harvesting vector supernatant from a stable producer cell line, wherein the vector supernatant is harvested about every 48 hours. In another aspect of the present disclosure is a method of harvesting vector supernatant from a stable producer cell line, wherein the vector supernatant is harvested every 40 to 56 hours.

In another aspect of the present disclosure is a method of harvesting vector supernatant comprising the LVsh5/C46 lentiviral vector, wherein the vector supernatant is harvest about every 48 hours.

In another aspect of the present disclosure is a stable producer cell line suitable for producing LVsh5/C46. In some embodiments, the stable producer cell line is based on the GPRG packaging cell line. In some embodiments, the stable producer cell line based on the GPRT packaging cell line. In some embodiments, the stable producer cell line based on the GPR packaging cell line. In some embodiments, the stable producer cell line based on the GPRT-G packaging cell line.

In another aspect of the present disclosure is a stable producer cell line suitable for producing a self-inactivating lentiviral vector having at least 90% identity to that of SEQ ID NO: 8. In some embodiments, the stable producer cell line is based on the GPRG packaging cell line. In some embodiments, the stable producer cell line based on the GPRT packaging cell line. In some embodiments, the stable producer cell line based on the GPR packaging cell line. In some embodiments, the stable producer cell line based on the GPRT-G packaging cell line.

In another aspect of the present disclosure is a concatemeric array comprising DNA fragments from a first plasmid and a second plasmid; the first plasmid derived from pUC57-TL20c; the second plasmid comprising a bleomycin antibiotic resistance cassette; wherein a ratio of the DNA fragments from the first plasmid to the second plasmid ranges from about 50:1 to about 1:50. In some embodiments, the ratio of the DNA fragments from the first plasmid to the second plasmid ranges from about 25:1 to about 1:25. In some embodiments, the ratio of the DNA fragments from the first plasmid to the second plasmid ranges from about 15:1 to about 1:15.

In another aspect of the present disclosure is a stable producer cell line, the stable producer cell line generated by transfecting a packaging cell line selected from the group consisting of GPR, GPRG, GPRT, GPRT-G and a derivative thereof with a concatemeric array, the concatemeric array comprising DNA fragments from a first plasmid and a second plasmid; the first plasmid derived from pUC57-TL20c; the second plasmid comprising a bleomycin antibiotic resistance cassette; wherein a ratio of the DNA fragments from the first plasmid to the second plasmid ranges from about 25:1 to about 1:25. In some embodiments, the stable producer cell line produces LVsh5/C46. In some embodiments, the LVsh5/C46 is capable of being harvested about every 48 hours.

In another aspect of the present disclosure is an isolated vector having the plasmid map of FIG. 11 which comprises a multiple cloning site that comprises the nucleotide sequence set forth in SEQ ID NO: 7.

In another aspect of the present disclosure is a kit comprising (1) a plasmid as described herein, and (2) a bleomycin resistance (ble) cassette. In some embodiments, the kit further comprises instructions for preparing a lentiviral vector and/or a concatemeric array, such as according to the procedures described herein.

In another aspect of the present disclosure is a kit comprising (a) a lentiviral transfer vector plasmid as described herein; and (b) a packaging cells. In some embodiments, the packaging cells are selected from the group consisting of GPR, GPRG, GPRT, GPRTG, and a derivative thereof. In some embodiments, the kit further comprises a bleomycin resistance (ble) cassette. In some embodiments, the kit further comprises instructions for preparing a lentiviral vector and/or a concatemeric array, such as according to the procedures described herein.

In another aspect of the present disclosure is a lentiviral vector derived from a plasmid as described herein. In some embodiments, the lentiviral vector comprises at least one additional nucleotide sequence. In some embodiments, the at least one additional nucleotide sequence is selected from the group consisting of a nucleotide sequence which encodes a short hairpin RNA for down-regulation of an HIV-1 co-receptor and a nucleotide sequence which encodes an HIV-1 fusion inhibitor. In some embodiments, the lentiviral vector is LVsh5/C46. In some embodiments, the lentiviral vector comprises a sequence having at least 95% identity to that of SEQ ID NO: 8.

In another aspect of the present disclosure is a pharmaceutical composition comprising the lentiviral vector described above and a pharmaceutically acceptable carrier. In some embodiments, the pharmaceutically acceptable carrier includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. Methods for the formulation of compounds with pharmaceutical carriers are known in the art and are described in, for example, in Remington's Pharmaceutical Science, (17th ed. Mack Publishing Company, Easton, Pa. 1985); and Goodman & Gillman's: The Pharmacological Basis of Therapeutics (11th Edition, McGraw-Hill Professional, 2005); the disclosures of each of which are hereby incorporated herein by reference in their entirety.

BRIEF DESCRIPTION OF THE DRAWINGS

FIG. 20A illustrates a flow cytometry analysis of 293T cells incubated with either fresh medium (left: no vector) or TL20-Cal1-WPRE (Right) harvested from the most potent producer clone. FIG. 20B illustrates a flow cytometry analysis of 293T cells incubated with either fresh medium (dark grey bar: no vector) or TL20-UbcGFP (light grey bar) harvested from the most potent producer clone. FIG. 20C illustrates the distribution of measured vector titers of supernatants from the independent producer clones for making the TL20-Cal1-WPRE (left) or TL20-UbcGFP (right) vector. The vectors were titrated on 293T cells and analyzed by flow cytometry. The highest titer achieved for the vectors prepared using polyclonal producer cells (before single clonal selection) is indicated by dashed line. Legend: Ubc: Ubiquitin C promoter; GFP: enhanced green fluorescence protein.

SEQUENCE LISTING

Figure 1:
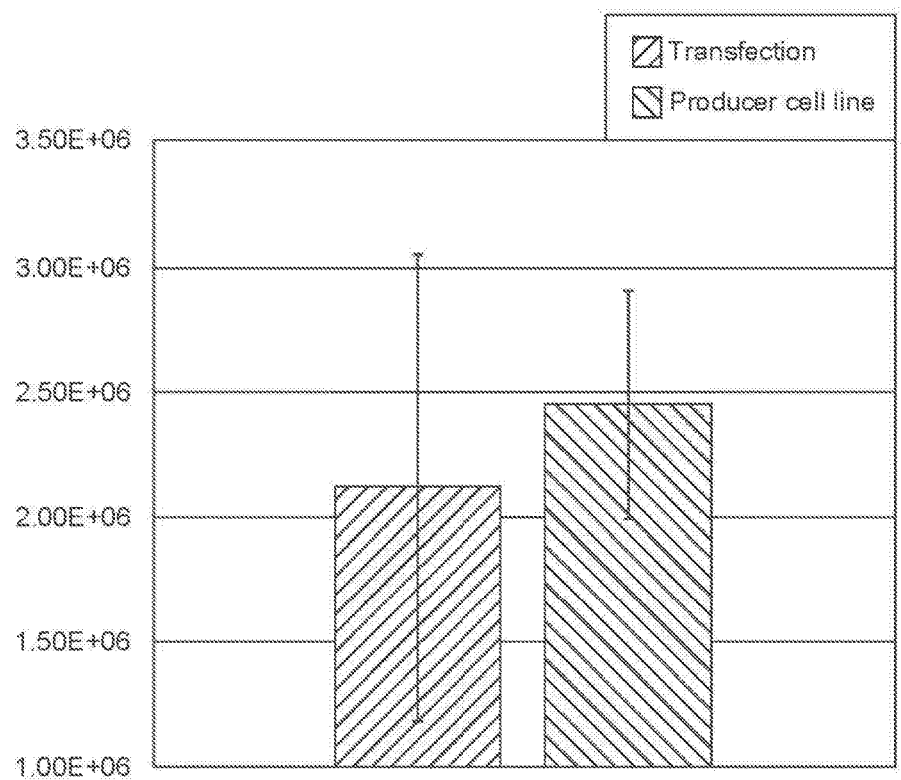
FIG. 1 illustrates that the same lentiviral vector was produced repeatedly by either transient transfection on HEK293T/17 cells according to established procedures, or using a GPRG-based stable producer cell line. Vector containing media (VCM) was concentrated 100× by ultracentrifugation and lentiviral (LV) titer was determined by gene transduction assay.

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "2016-05-09_Cal-0013WO_ST25.txt" created on May 9, 2016, 5 KB, which is incorporated by reference herein.

DETAILED DESCRIPTION

In general, the present disclosure provides a method of generating a stable producer cell line. The generation of stable producer cell lines, such as those provided in accordance with the present invention, increases the reproducibility and ease of creating high titer lentiviral stocks while easing biosafety concerns and the variation in expressed envelope proteins defines the tropism of the generated virus. The present disclosure also provides for a novel lentiviral transfer vector plasmid.

As used herein, the singular terms "a," "an," and "the" include plural referents unless the context clearly indicates otherwise. Similarly, the word "or" is intended to include "and" unless the context clearly indicates otherwise.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "cloning" refers to the process of ligating a nucleic acid molecule into a plasmid and transferring it into an appropriate host cell for duplication during propagation of the host.

As used herein, the term "HIV" includes not only HIV-1, but also the various strains of HIV-1 (e.g. strain BaL or strain SF162) and the various subtypes of HIV-1 (e.g. subtypes A, B, C, D, F, G H, J, and K).

As used herein, the term "multiple cloning site" (MCS) refers to nucleotide sequences comprising restriction sites for the purpose of cloning nucleic acid fragments into a cloning vector plasmid. A MCS, also referred to as a polylinker or polycloning site, is a cluster of cloning sites such that many restriction enzymes are able to operate within the site. A cloning site in some embodiments is a known sequence upon which a restriction enzyme operates to linearize or cut a plasmid.

As used herein, the term "producer cell" refers to a cell which contains all the elements necessary for production of lentiviral vector particles.

As used herein, the term "packaging cell" refers to a cell which contains those elements necessary for production of infectious recombinant virus which are lacking in a recombinant viral vector or lentiviral transfer vector plasmid. Typically, such packaging cells contain one or more expression cassettes which are capable of expressing viral structural proteins (such as gag, pol and env) but they do not contain a packaging signal.

As used herein, the terms "restriction endonuclease" or "restriction enzyme" refer to a member or members of a class of catalytic molecules that bind a cognate sequence of a nucleic acid molecule (e.g. DNA) and cleave it at a precise location within that sequence.

As used herein, the term "self-inactivating" or "SIN," used interchangeably herein, refers to a vector which is modified, wherein the modification greatly reduces the ability of the vector to mobilize once it has integrated into the genome of the recipient, thereby increasing the safety of the use of the vector as a gene delivery vector.

As used herein, the term "vector" refers to a nucleic acid molecule capable of mediating entry of, e.g., transferring, transporting, etc., another nucleic acid molecule into a cell. The transferred nucleic acid is generally linked to, e.g., inserted into, the vector nucleic acid molecule. A vector may include sequences that direct autonomous replication, or may include sequences sufficient to allow integration into host cell DNA. As will be evident to one of ordinary skill in the art, viral vectors may include various viral components in addition to nucleic acid(s) that mediate entry of the transferred nucleic acid.

Overview of Method

Lentiviral vectors (LVs) are important tools for gene transfer due to their efficiency and ability to stably transduce both dividing and non-dividing cells. As a result, investigators are using them as gene delivery vehicles in a wide variety of clinical applications. Nevertheless, large-scale clinical production using current good manufacturing practice (cGMP) methods comes with a set of challenges that must be considered as more clinical trials using lentiviral vectors receive regulatory approval. One important consideration in designing cGMP-compatible processes is the need to integrate regulatory considerations into manufacturing processes that are capable of producing consistent lentivirus for multiple cGMP productions. The vast majority of lentiviral vectors being used clinically has been produced by transient transfection. Transient transfection based production is, however, often labor intensive and subject to variation. For this reason, several stable packaging cell line systems have recently been developed. While the use of these cell lines for the bio-manufacturing of LV is particularly attractive for both scalability and consistency, development of such lines is time consuming and the regulatory pathway for the cGMP use of these lines has not been firmly established.

In view of this, the present disclosure sets forth a process for the clinical production of self-inactivating lentiviral vectors (SIN-LVs). It is believed that through the use of a novel lentiviral transfer vector plasmid together with GPR, GPRG, GPRT, GPRGT or GPRT-G packaging cell lines (or a derivative or analog packaging cell line derived therefrom), that stable producer cell lines may be generated so as to enable the production of self-inactivating lentiviral vectors (e.g. LVsh5/C46). While certain embodiments and examples described herein refer to the production of LVsh5/C46, which is a self-inactivating lentiviral vector encoding a short hairpin RNA (shRNA) for down-regulation of the HIV-1 co-receptor CCR5, in combination with a HIV-1 fusion inhibitor (namely, C46), the skilled artisan will recognize that the methods described herein are suitable for the generation of stable producer cell lines capable of producing any SIN-LVs, comprising any desired or client supplied genes or sequences.

Applicants have demonstrated that compared to SIN-LVs produced by transient transfection, that the presently disclosed method (i) is capable of generating a similar quality and quantity of SIN-LVs; (ii) produces LVs that may have better potency; and (ii) maintains yields while greatly decreasing prep-to-prep variability seen with transient transfection.

pUC57-TL20c

In one aspect of the present disclosure is a human immunodeficiency virus type 1 (HIV-1) based third generation, self-inactivating (SIN) lentiviral transfer vector plasmid (hereinafter referred to as "pUC57-TL20") comprising a novel, versatile multiple cloning site (MCS) (see FIG. 11).

Figure 12:
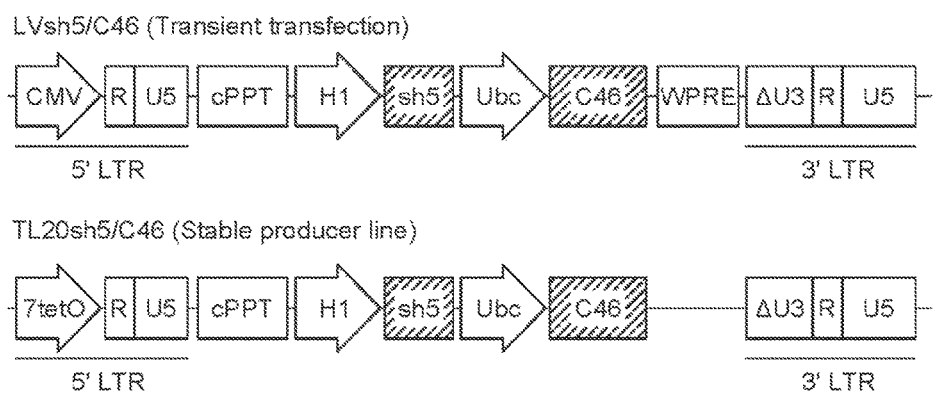
FIG. 12 illustrates an HIV-1 based lentiviral transfer vector according to some embodiments of the present disclosure. This particular transfer vector encodes a short hairpin RNA (shRNA) for down-regulation of the HIV-1 co-receptor CCR5, in combination with a HIV-1 fusion inhibitor (C46).
Figure 13:
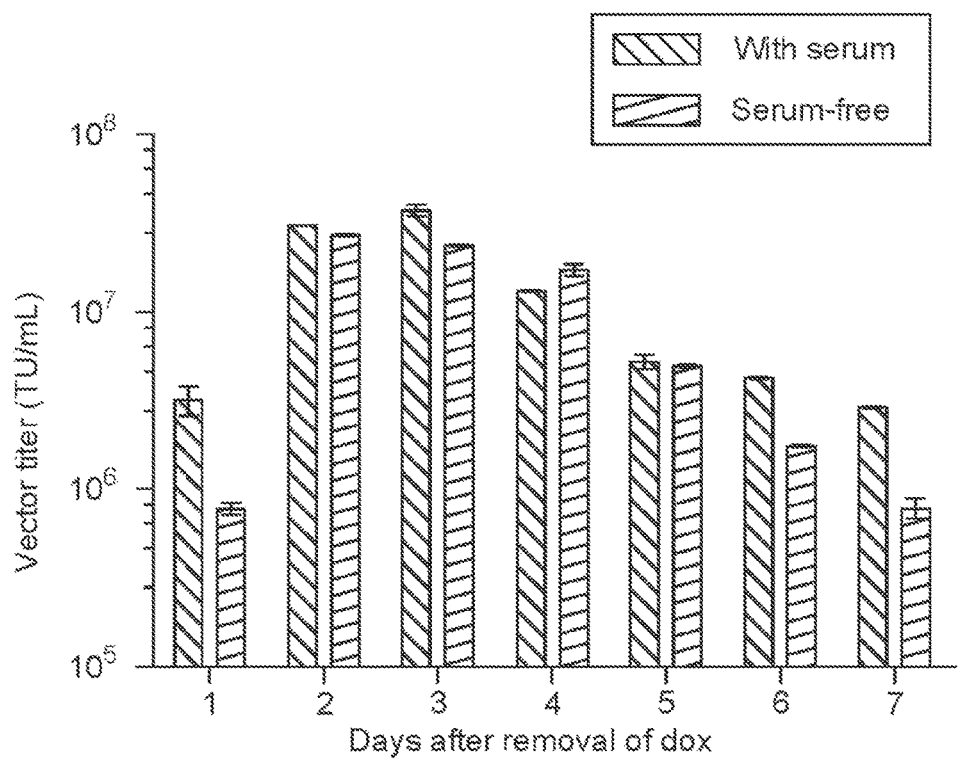
FIG. 13 illustrates lentiviral induction from using the methods disclosed herein with and without serum. Cells cultured in serum-free media produced nearly as much virus as those cultured with 10% PBS. It is believed that the methods disclosed here may be adapted to serum-free culture environments.

In some embodiments, the lentiviral vector transfer plasmid comprises a vector backbone ("TL20c") that does not itself comprise an internal promoter (hence, it is "promoterless"). In some embodiments, the lentiviral vector transfer plasmid comprises one promoter, e.g. a tetracycline repressible promoter, upstream of the vector backbone (see FIG. 12). Without wishing to be bound by any particular theory, it is believed that the promoterless design of the vector backbone allows for the generation of a lentiviral transfer vector plasmid that enables the delivery and subsequent expression of a gene of interest from a user-determined promoter.

Figure 11:
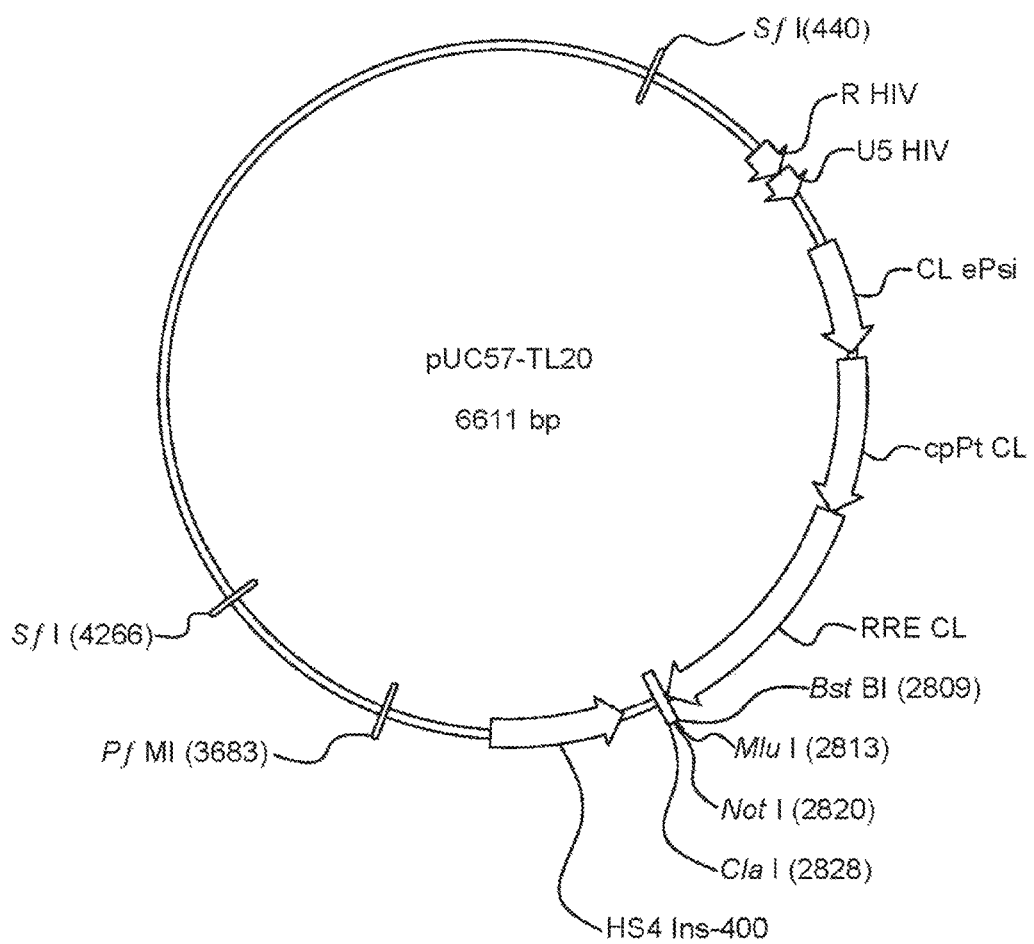
FIG. 11 sets forth a schematic diagram of pUC57-TL20.

FIG. 11 sets forth a gene map illustrating the constituent elements of the lentiviral vector transfer plasmid. In some embodiments, the lentiviral vector transfer plasmid comprises between about 6500 nucleotides and about 6750 nucleotides. In other embodiments, the lentiviral vector transfer plasmid comprises between 6600 nucleotides and about 6700 nucleotides. In some embodiments, the vector backbone of the lentiviral transfer vector plasmid comprises between about 3850 nucleotides and about 3950 nucleotides. In some embodiments, the vector backbone of the lentiviral transfer vector plasmid comprises about 3901 nucleotides.

As shown in FIG. 11, the plasmid comprises a 5' flanking HIV LTR, a packaging signal or ψ+, a central polypurine tract (cPPT), a Rev-response element (RRE), a multiple cloning site (MCS), and a 3' flanking HIV LTR. The LTR regions further comprise a U3 and U5 region, as well as an R region.

According to certain embodiments of the disclosure, the transfer plasmid includes a self-inactivating (SIN) LTR. As is known in the art, during the retroviral life cycle, the U3 region of the 3' LTR is duplicated to form the corresponding region of the 5' LTR in the course of reverse transcription and viral DNA synthesis. Creation of a SIN LTR is achieved by inactivating the U3 region of the 3' LTR (preferably by deletion of a portion thereof, e.g. removal of a TATA sequence). The alteration is transferred to the 5' LTR after reverse transcription, thus eliminating the transcriptional unit of the LTRs in the provirus, which is believed to prevent mobilization by replication competent virus. An additional safety enhancement is provided by replacing the U3 region of the 5' LTR with a heterologous promoter to drive transcription of the viral genome during production of viral particles.

In some embodiments, the packaging signal comprises about 361 base pairs of the Gag sequence and about 448 base pairs of the Pol sequence of wild-type HIV (e.g. HIV01 HXB2_LAI_IIIB). In some embodiments, the cPPT comprises about 85 base pairs of the Vif sequence of wild-type HIV. In some embodiments, a HIV Polypurine tract (pPu) comprises about 106 base pairs of the Nef sequence of wild-type HIV. In some embodiments, the RRE comprises about 26 base pairs of the Rev sequence, about 25 base pairs of the tat sequence, and about 769 base pairs of the Env sequence of wild-type HIV. In some embodiments, the transfer plasmid comprises a chromatin insulator and/or a beta-globulin polyadenylation signal.

In some embodiments, the nucleotide sequence encoding the packing signal comprises the sequence of SEQ ID NO: 3, or a sequence having at least 85% identity to that of SEQ ID NO: 3. In some embodiments, the nucleotide sequence encoding the packing signal comprises the sequence of SEQ ID NO: 3, or a sequence having at least 90% identity to that of SEQ ID NO: 3. In some embodiments, the nucleotide sequence encoding the packing signal comprises the sequence of SEQ ID NO: 3, or a sequence having at least 95% identity to that of SEQ ID NO: 3.

In some embodiments, the nucleotide sequence encoding the central polypurine tract (cPPT) comprises the sequence of SEQ ID NO: 4, or a sequence having at least 85% identity to that of SEQ ID NO: 4. In some embodiments, the nucleotide sequence encoding the central polypurine tract (cPPT) comprises the sequence of SEQ ID NO: 4, or a sequence having at least 90% identity to that of SEQ ID NO: 4. In some embodiments, the nucleotide sequence encoding the central polypurine tract (cPPT) comprises the sequence of SEQ ID NO: 4, or a sequence having at least 95% identity to that of SEQ ID NO: 4.

In some embodiments, the nucleotide sequence encoding the Rev response element comprises the sequence of SEQ ID NO: 5, or a sequence having at least 85% identity to that of SEQ ID NO: 5. In some embodiments, the nucleotide sequence encoding the Rev response element comprises the sequence of SEQ ID NO: 5, or a sequence having at least 90% identity to that of SEQ ID NO: 5. In some embodiments, the nucleotide sequence encoding the Rev response element comprises the sequence of SEQ ID NO: 5, or a sequence having at least 95% identity to that of SEQ ID NO: 5.

In some embodiments, the nucleotide sequence encoding the self-inactivating long terminal repeat comprises the sequence of SEQ ID NO: 6, or a sequence having at least 85% identity to that of SEQ ID NO: 6. In some embodiments, the nucleotide sequence encoding the self-inactivating long terminal repeat comprises the sequence of SEQ ID NO: 6, or a sequence having at least 90% identity to that of SEQ ID NO: 6. In some embodiments, the nucleotide sequence encoding the self-inactivating long terminal repeat comprises the sequence of SEQ ID NO: 6, or a sequence having at least 95% identity to that of SEQ ID NO: 6.

In some embodiments, the plasmid comprises a nucleotide sequence encoding a doxycycline repressible promoter that has at least 85% identity to that of SEQ ID NO: 10. In some embodiments, the plasmid comprises a nucleotide sequence encoding a doxycycline repressible promoter that has at least 90% identity to that of SEQ ID NO: 10. In some embodiments, the plasmid comprises a nucleotide sequence encoding a doxycycline repressible promoter that has at least 95% identity to that of SEQ ID NO: 10.

In some embodiments, the plasmid comprises a nucleotide sequence encoding an HIV LTR R5 region that has at least 85% identity to that of SEQ ID NO: 11. In some embodiments, the plasmid comprises a nucleotide sequence encoding an HIV LTR R5 region that has at least 90% identity to that of SEQ ID NO: 11. In some embodiments, the plasmid comprises a nucleotide sequence encoding an HIV LTR R5 region that has at least 95% identity to that of SEQ ID NO: 11.

In some embodiments, the plasmid comprises a nucleotide sequence encoding an HIV LTR U5 region that has at least 85% identity to that of SEQ ID NO: 12. In some embodiments, the plasmid comprises a nucleotide sequence encoding an HIV LTR U5 region that has at least 90% identity to that of SEQ ID NO: 12. In some embodiments, the plasmid comprises a nucleotide sequence encoding an HIV LTR U5 region that has at least 95% identity to that of SEQ ID NO: 12.

In some embodiments, the plasmid comprises a nucleotide sequence encoding a chromatin insulator that has at least 85% identity to that of SEQ ID NO: 13 In some embodiments, the plasmid comprises a nucleotide sequence encoding a chromatin insulator that has at least 90% identity to that of SEQ ID NO: 13. In some embodiments, the plasmid comprises a nucleotide sequence encoding a chromatin insulator that has at least 95% identity to that of SEQ ID NO: 13.

In some embodiments, the plasmid comprises a nucleotide sequence encoding a beta-globin polyadenylation signal that has at least 85% identity to that of SEQ ID NO: 14. In some embodiments, the plasmid comprises a nucleotide sequence encoding a beta-globin polyadenylation signal that has at least 90% identity to that of SEQ ID NO: 14. In some embodiments, the plasmid comprises a nucleotide sequence encoding a beta-globin polyadenylation signal that has at least 95% identity to that of SEQ ID NO: 14.

In some embodiments, the plasmid comprises a nucleotide sequence that has at least 85% identity to that of SEQ ID NO: 15. In some embodiments, the plasmid comprises a nucleotide sequence that has at least 90% identity to that of SEQ ID NO: 15. In some embodiments, the plasmid comprises a nucleotide sequence that has at least 95% identity to that of SEQ ID NO: 15.

The disclosure provides lentiviral transfer vector plasmids incorporating a MCS for a variety of different restriction enzymes. According to certain embodiments of the disclosure, the MCS comprises a sequence having between about 20 and 40 nucleotides. In some embodiments, the MCS of the presently disclosed plasmid comprises at least two restriction enzyme cutting sites. In other embodiments, the MCS of the presently disclosed plasmid comprises at least three restriction enzyme cutting sites. In yet other embodiments, the MCS of the presently disclosed plasmid comprises between about 2 and about 10 restriction sites. In some embodiments, the restriction sites within the MCS are selected from the group consisting of BstBI, MluI, NotI, ClaI, ApaI, XhoI, XbaI, HpaI, NheI, PacI, NsiI, SphI, Sma/Xma, AccI, BamHI, and SphI, or any derivatives or analog thereof.

In some embodiments, the MCS region of the lentiviral transfer vector plasmid carries four unique restriction enzyme cutting sites which are believed to facilitate easy sub-cloning of a desired transgene cassette. In some embodiments, the multiple cloning site comprises the BstBI, MluI, NotI, and ClaI restriction endonuclease sites. In some embodiments, the nucleotide sequence encoding the multiple cloning site comprises the sequence of SEQ ID NO: 7, or a sequence having at least 90% identity to that of SEQ ID NO: 7. There restriction site may be arranged in any order.

In some embodiments, the transfer plasmid comprises one or more additional restriction enzyme cutting sites flanking the vector backbone (see FIG. 11). Without wishing to be bound by any particular theory, it is believed that the additional flanking restriction enzyme cutting sites allow for the generation of a directional (a "head-to-tail") concatemeric array. In some embodiments, the restriction enzyme cutting sites are selected from SfiI and Bsu36I. In some embodiments, a lentiviral vector comprising one or more genes is derived from the plasmid.

In some embodiments, the lentiviral vector transfer plasmid comprises a nucleotide sequence having at least 80% identity to that of sequence of SEQ ID NO: 1. In other embodiments, the lentiviral vector transfer plasmid comprises a nucleotide sequence having at least 85% identity to that of sequence of SEQ ID NO: 1. In yet other embodiments, the lentiviral vector transfer plasmid comprises a nucleotide sequence having at least 90% identity to that of sequence of SEQ ID NO: 1. In further embodiments, the lentiviral vector transfer plasmid comprises a nucleotide sequence having at least 95% identity to that of sequence of SEQ ID NO: 1. In yet further embodiments, the lentiviral vector transfer plasmid comprises a nucleotide sequence having at least 97% identity to that of sequence of SEQ ID NO: 1. In some embodiments, the lentiviral vector transfer plasmid comprises the sequence of SEQ ID NO: 1. In some embodiments, the lentiviral vector transfer plasmid has a sequence that differs by not more than 100 nucleotides from the sequence set forth in SEQ ID NO: 1.

In some embodiments, the lentiviral transfer vector plasmid comprises a nucleotide sequence having at least 80% identity to that of sequence of SEQ ID NO: 2. In other embodiments, the lentiviral vector transfer plasmid comprises a nucleotide sequence having at least 85% identity to that of sequence of SEQ ID NO: 2. In yet other embodiments, the lentiviral vector transfer plasmid comprises a nucleotide sequence having at least 90% identity to that of sequence of SEQ ID NO: 2. In further embodiments, the lentiviral vector transfer plasmid comprises a nucleotide sequence having at least 95% identity to that of sequence of SEQ ID NO: 2. In yet further embodiments, the lentiviral vector transfer plasmid comprises a nucleotide sequence having at least 97% identity to that of sequence of SEQ ID NO: 2. In some embodiments, the lentiviral vector transfer plasmid comprises the sequence of SEQ ID NO: 2. In some embodiments, the lentiviral vector transfer plasmid has a sequence that differs by not more than 100 nucleotides from the sequence set forth in SEQ ID NO: 2.

In some embodiments, the lentiviral transfer vector plasmid is synthesized according to those methods known to those of skill in the art. For example, the plasmids may be synthesized using traditional restriction digestion and ligation techniques known to those of ordinary skill in the art. For example, a donor plasmid comprising the TL20c vector backbone may be subcloned into a pU57C recipient plasmid (e.g. such as those available commercially from Genescript), using standard digestion and ligation procedures known to those of ordinary skill in the art (see, for example, Sambrook et al. (1989) Molecular Cloning: A Laboratory Manual, 2nd Ed. Cold Spring Harbor, N.Y., the disclosure of which is hereby incorporated by reference herein in its entirety).

The present disclosure also includes a method of producing a lentiviral vector, e.g. LVsh5/C46. In one embodiment, the method comprises synthesizing a cDNA of a gene and cloning the synthesized cDNA into a restriction site of a plasmid, such as pUC57-TL20c. Genes may be inserted into an appropriate cloning site using techniques known to those of skill in the art. For example, a gene may be amplified by PCR and then cloned into a plasmid containing a desired promoter or gene-expression controlling element.

In some embodiments, and solely by way of example, the method comprises synthesizing a cDNA of a gene which expresses a protein capable of preventing HIV fusion into a cell or HIV replication; and then cloning the synthesized cDNA into a restriction site in a plasmid as disclosed herein.

Figure 2:
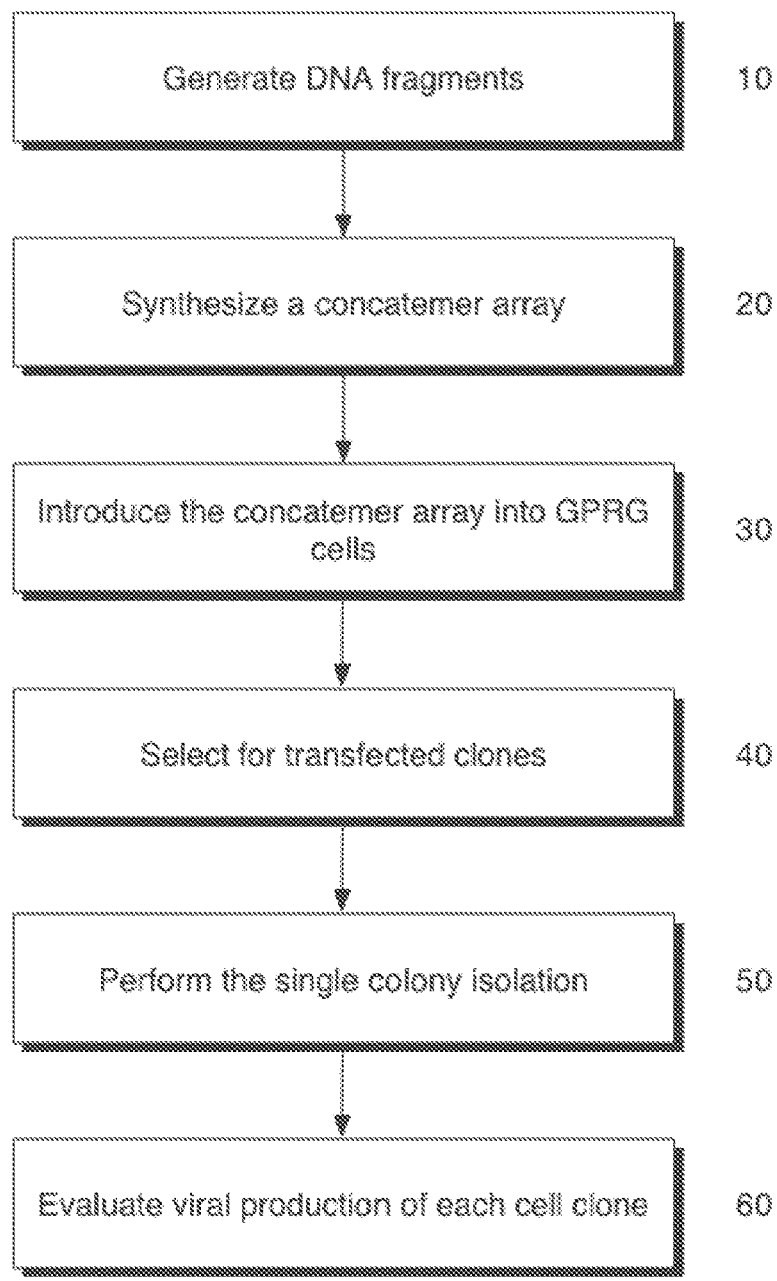
FIG. 2 is a flowchart illustrating a method of generating a stable producer cell line and for harvesting lentiviral vectors produced from the generated stable producer cell line.

Generation of a Stable Producer Cell Line and Harvesting of Lentiviral Vectors Produced Therefrom In some embodiments of the present disclosure are methods of forming a stable producer cell line and harvesting lentiviral vectors produced from the generated stable producer cell line. With reference to FIG. 2, the first step in producing a stable producer cell line is to generate DNA fragments (10), such as from a lentiviral vector transfer plasmid and a second plasmid, such as an antibiotic resistance cassette plasmid. Following DNA fragment generation (10), the DNA is then used to form a concatemeric array (20). Subsequently, the concatemeric array is then introduced, such as by transfection, into a packing cell line (30) (e.g. GPR, GPRG, GPRT, GPRG, GPRT-G or derivatives thereof packaging cell lines). Following introduction of the array (30) and subsequent transfection, clones are selected (40) and isolated (50) to generate the stable producer cell line (60). Vector supernatant comprising lentiviral vector may then be harvested.

Concatemeric Array Formation and Purification

A "concatemer" or "concatemeric array" (used interchangeably herein) (a long continuous DNA molecule that contains multiple copies of the same DNA sequences linked directly or indirectly in series) is generated and used in the transfection of the packaging cell line. In some embodiments, the concatemers are large arrays of linked vector genome expression cassettes, with antibiotic resistance cassettes interspersed therein.

Figure 14:
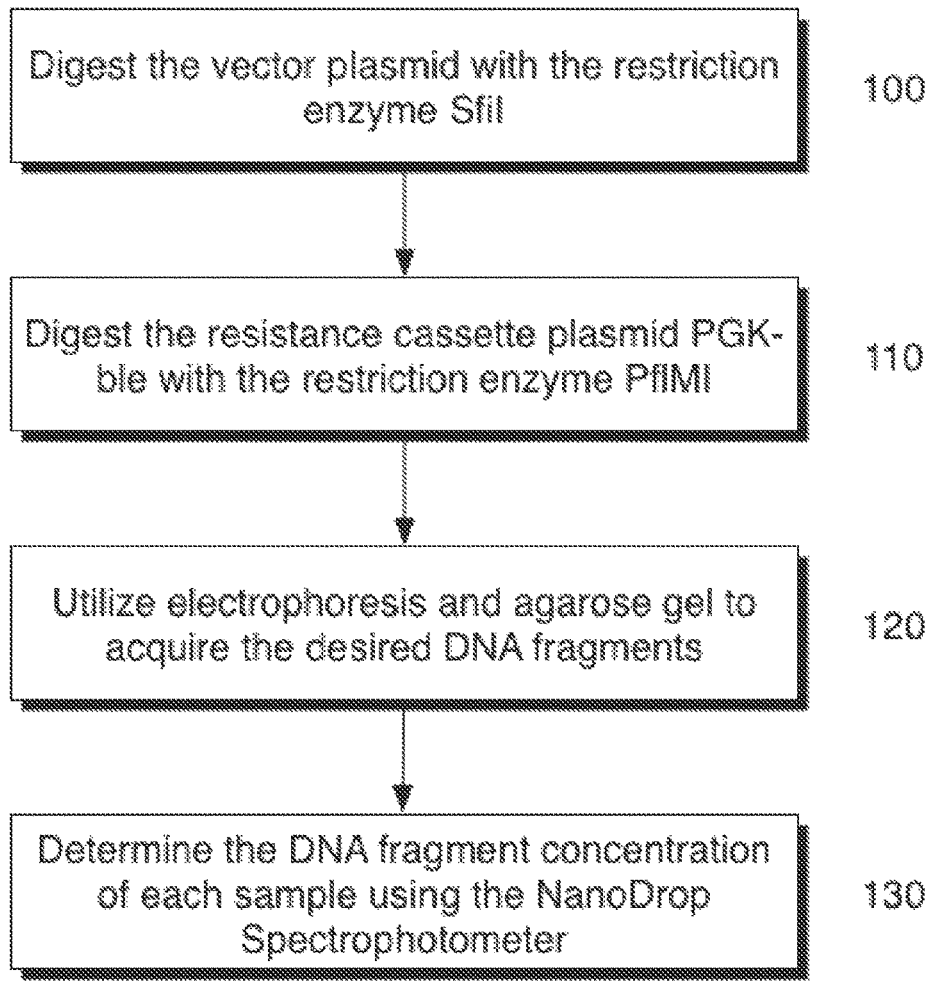
FIG. 14 is a flowchart illustrating a method of generating DNA fragments.

With reference to FIG. 14, to form the concatemeric array, DNA fragments from a lentiviral transfer vector plasmid (step 100) and an antibiotic resistance cassette plasmid are generated (step 110). In some embodiments, the DNA fragments may be prepared by digesting each of the plasmids according to protocols known to those of ordinary skill in the art and then ligating the digested fragments. In some embodiments, electrophoresis and agarose gel are utilized to acquire the desired DNA fragments (step 120). In some embodiments, a DNA fragment concentration may be determined using a NanoDrop Spectrophotometer (step 130). A variety of strategies are available for ligating fragments of DNA, the choice of which depends on the nature of the termini of the DNA fragments and which choices can be readily made by the skilled artisan.

In some embodiments, the lentiviral transfer vector plasmid is based on pUC57-TL20c. In some embodiments, the antibiotic resistance cassette plasmid is driven by the PGK promoter. In some embodiments, the antibiotic resistance cassette plasmid comprises flanking sites for concatemerization with the lentivirus cassette in the lentiviral transfer vector plasmid. In some embodiments, the antibiotic resistance cassette plasmid is PGK-ble (bleomycin resistance). In some embodiments, the PGK-ble plasmid comprises a nucleotide sequence having at least 90% identity to the sequence of SEQ ID NO: 9. In some embodiments, the concatemeric arrays is formed through the in vitro ligation of the DNA fragments from the lentiviral transfer vector plasmid and the PGK-ble plasmid.

Figure 15:
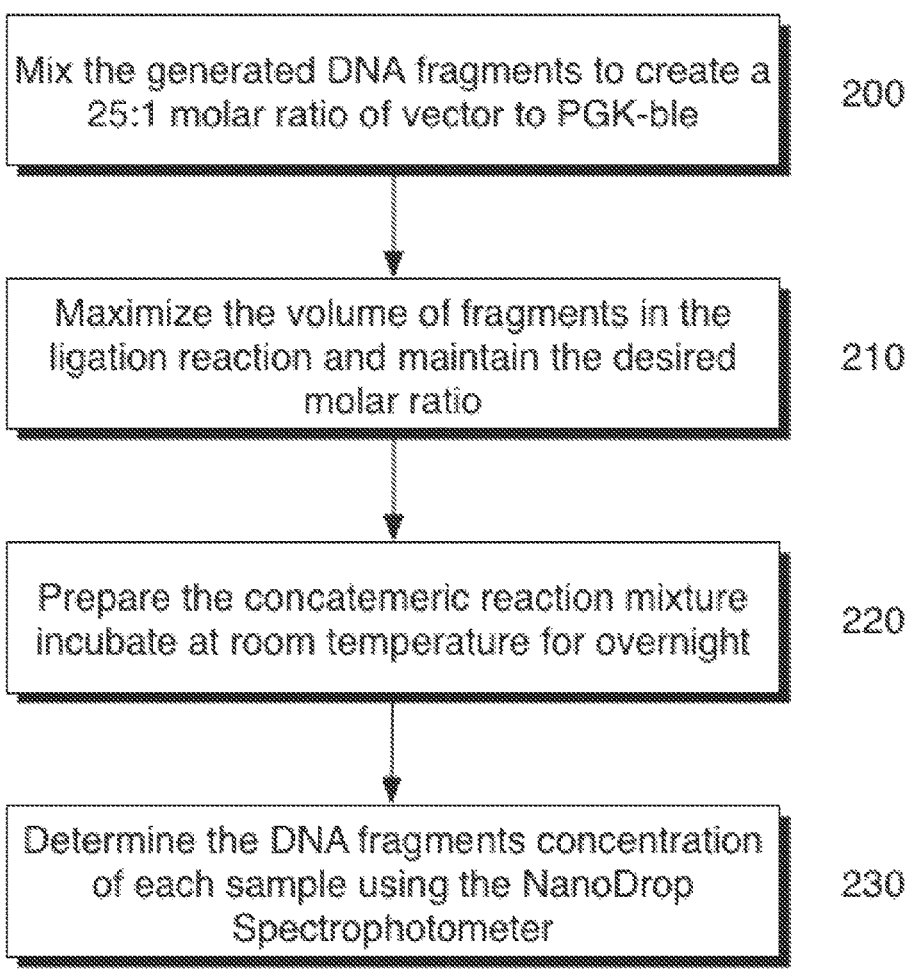
FIG. 15 is a flowchart illustrating a method of synthesizing a concatemeric array.

FIG. 15 outlines the general steps used to form the concatemeric array. At step 200, generated DNA fragments are mixed and the volume of fragments in the ligation reaction are maximized to maintain the desired ratio (step 210). In some embodiments, a ratio of an amount of lentiviral transfer vector plasmid DNA to an amount of antibiotic resistance cassette plasmid DNA ranges from about 100:1 to about 1:100. In other embodiments, a ratio of an amount of lentiviral transfer vector plasmid DNA to an amount of antibiotic resistance cassette plasmid DNA ranges from about 50:1 to about 1:50. In yet other embodiments, a ratio of an amount of lentiviral transfer vector plasmid DNA to an amount of antibiotic resistance cassette plasmid DNA ranges from about 25:1 to about 1:25. In further embodiments, a ratio of an amount of lentiviral transfer vector plasmid DNA to an amount of antibiotic resistance cassette plasmid DNA ranges from about 10:1 to about 1:10.

In some embodiments, the concatemeric reaction mixture is incubated overnight at room temperature (step 220). Subsequently, the DNA fragment concentration for each sample may then be measured using a NanoDrop Spectrophotometer (step 230).

In some embodiments, a directional concatemeric array is formed and used in the transfection of a packing cell line. In some embodiments, the formation of the directional array is achieved by utilizing the restriction enzyme sites of the lentiviral transfer vector plasmid which flank the lentiviral vector backbone. In some embodiments, restriction digestion utilizes the restriction enzyme sites flanking the TL20c vector cassette and allows for the formation of nucleotide nonpalindromic overhangs, which can only be used to ligate from heat to tail. In some embodiments, directional ligation, according to the methods described herein, allow for the generation of a concatemeric array which comprises predominantly head-to-tail DNA products.

In some embodiments, the concatemeric array is formed according to the method set forth in Example 3 herein. Of course, the skilled artisan will recognize that the procedure provided in Example 3 may be adapted for the formation of a concatemeric array having different ratios of a first plasmid to a second plasmid and for transfer plasmids other than LVsh5/C46.

In some embodiments, the concatemeric array is purified by phenol-extraction and ethanol precipitation prior to transfection into a packing cell line. While this conventional technique is cheap and effective, however, the procedure is time consuming and may not yield reproducible yields. There is believed to be a risk of phenol/chloroform carry-over into the final sample. Moreover, the process is believed to involve hazardous chemicals and may generate toxic waste that must be disposed of with care and in accordance with hazardous waste guidelines.

Alternatively, in other embodiments, a silica-based method is used to purify the newly synthesized concatemeric array after ligation. This method is believed to provide a simple, reliable, fast, and convenient way for isolation of the high-quality transfection-grade concatemeric array. In some embodiments, the concatemeric array is purified using a DNeasy Mini spin column, available from Qiagen, such as using the procedure set forth in Example 6.

Transfection/Single Clone Isolation

Following purification of the concatemeric array, the array is then used to transfect packaging cell line cells. As used herein, the terms "transformation" and "transfection" are intended to refer to a variety of art-recognized techniques for introducing foreign nucleic acid (e.g., DNA or RNA) into cells. As will be evident from the examples provided herein, when a host cell permissive for production of lentiviral particles is transfected with the generated concatemeric array, the cell becomes a producer cell, i.e. a cell that produces infectious lentiviral particles.

Figure 16:
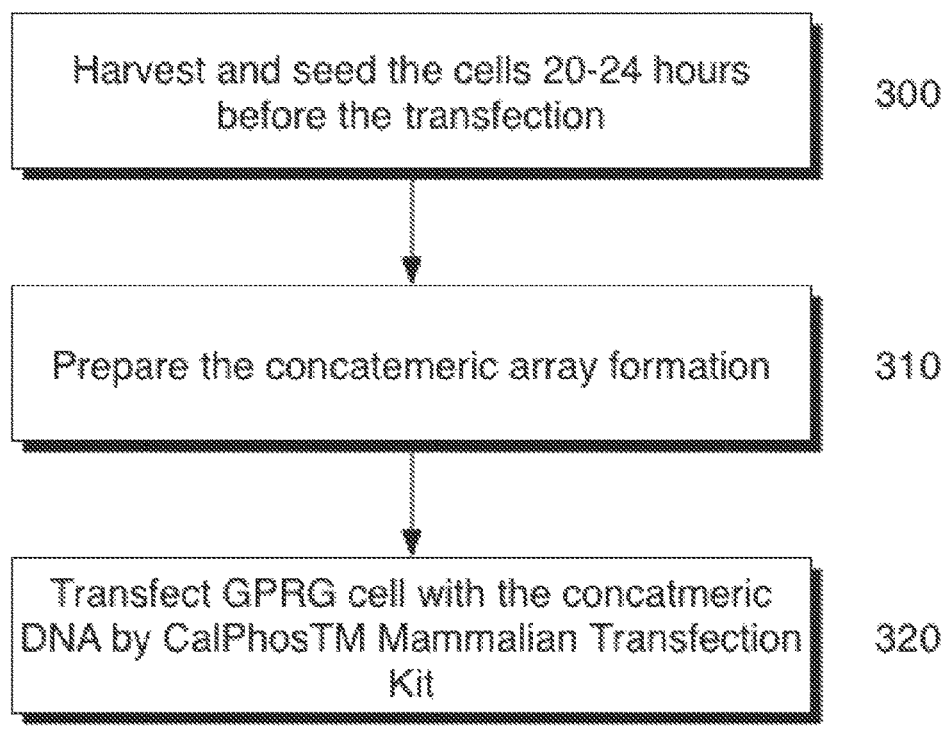
FIG. 16 is a flowchart illustrating a method of introducing a concatemeric array into a packaging cell line.

In general, the concatemeric array or directional concatemeric array may be introduced into cells via conventional transfection techniques. With reference to FIG. 16, in some embodiments, cells are harvested and seeded 20-24 hours before transfection (step 300) and then transfected (step 320) with the concatemeric array synthesized (step 310). A procedure for transfecting a packing cell line cell is provided as Example 4 herein.

One packaging cell line suitable for transfection with the formed concatemeric arrays is the GPR packaging cell line. The GPR line is an HIV-1-based packaging cell line derived from 293T/17 cells with the necessary viral components gagpol and rev (see, Throm et al., Efficient construction of producer cell lines for a SIN lentiviral vector for SCID-X1 gene therapy by concatemeric array transfection. Blood 113: 5104-5110, the disclosure of which is hereby incorporated by reference herein in its entirety).

Another packaging cell line suitable for transfection with the formed concatemeric arrays is a GPRG packaging cell line. In some embodiments, the GPRG packing cell line comprises gagpol, rev, and VSV-G.

Yet another packaging cell line suitable for transfection with the formed concatemeric arrays is a GPRT packaging cell line (gagpol, rev, and tat). GPRG and GPRT packaging cell lines and methods of forming the same are also disclosed by Throm et. al, the disclosure of which is again hereby incorporated by reference herein in its entirety. Other suitable packaging cell lines (e.g. GPRT-G) are described by Wielgosz et al. "Generation of a lentiviral vector producer cell clone for human Wiskott-Aldrich syndrome gene therapy," Molecular Therapy—Methods & Clinical Development 2, Article number: 14063 (2015), the disclosure of which is hereby incorporated by reference herein in its entirety.

The skilled artisan will appreciate that other packaging cell lines suitable for use with the presently disclosed method may also be utilized. In some embodiments, other packaging cell lines may be derived from the GPR, GPRG, GPRT, or GPRT-G packaging cell lines. Without wishing to be bound by any particular theory, it is believed that the GPRT-G cell line has higher transduction efficiency in CD34+ cells (see Wielgosz). By "derived from," what is meant is a population of cells clonally descended from an individual cell and having some select qualities, such as the ability to produce active protein at a given titer, or the ability to proliferate to a particular density.

Figure 17:
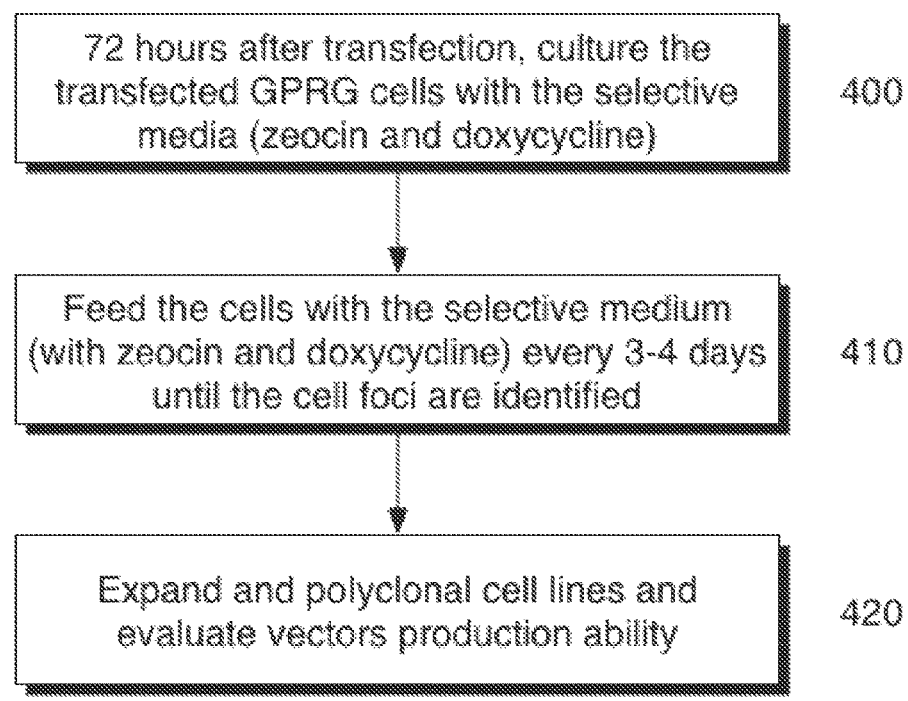
FIG. 17 is a flowchart illustrating a method of selecting for transfected clones.

FIG. 17 illustrates the general process of selecting for transfected cells. In some embodiments, and after about 72 hours after transfection, GPRG cells are cultured with the selective media (zeocin and doxycycline) (step 400). The cells are then fed with selective medium (zeocin and doxycycline) every 3-4 days until the cell foci are identified (step 410). Subsequently, the cell lines are expanded and evaluated (step 420).

In some embodiments, following transfection a single foci selection/screening process is utilized to identify the single cell clones that have good manufacturing potential. According to this method, in some embodiments, selected cells are seeded sparsely in 150×25 mm dishes and allowed to expand and form discernible colonies for 2-3 weeks. The individual colonies can then be transferred to another smaller culture vessel for monoclonal expansion. This method is believed to be a cost-effective and frequently adopted technique; however, due to the nature limitations in the single foci selection technique, achieving a high probability of monoclonality of a good producing cell line may be challenging.

Figure 18:
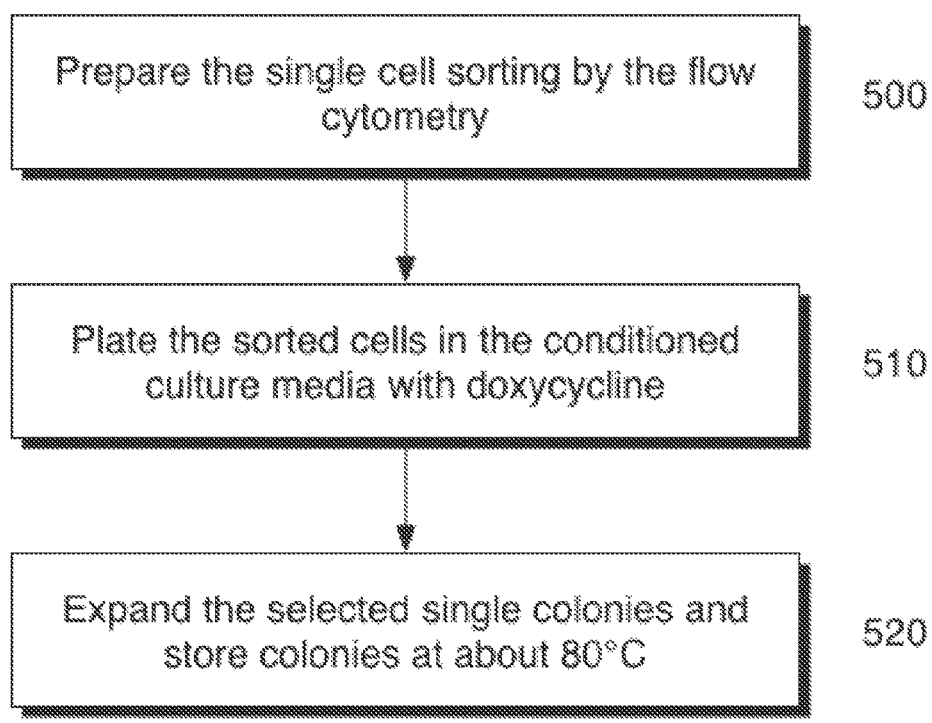
FIG. 18 is a flowchart illustrating a method of performing a single colony isolation.

FIG. 18 illustrates single colony isolation. At step 500, flow cytometry is utilized to prepare the single cell sorting. The cells are then plated (step 510) in the conditioned culture media, and expanded (step 520).

Figure 8:
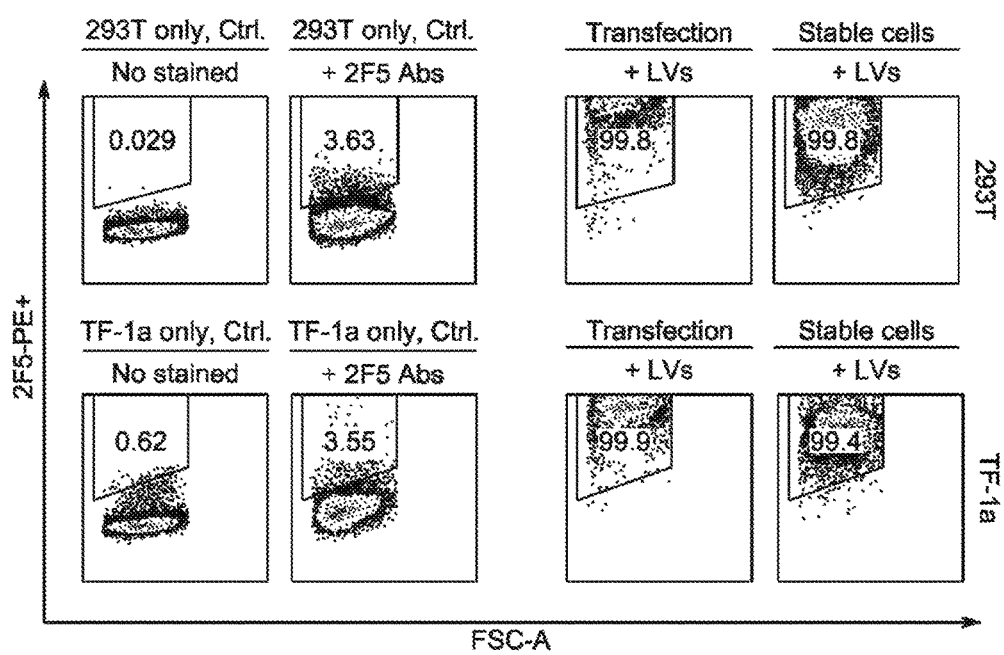
FIG. 8 sets forth a FACS analysis of 293T or TF-1a cells incubated with either fresh medium (no vector) or LVsh5/C46 vectors.

In other embodiments, in order to generate a high titer lentiviral vector stable producer cell line, Fluorescence activated cell sorter (FACS) have been used to isolate single clones (see, e.g. FIG. 8). Conditioned medium, e.g. Zeocin (50 ug/mL) and Doxycycline (1 ng/mL), may also be added during a sorting process to increase cell attachment and viability, and promote colony formation. The use of conditioned growth media and the high throughput ability of FACS system is believed to enable the screening a large number of clones and thus is believed to increases the probability of finding high titer lentiviral vector producer clones.

In some embodiments, a clone with good growing rate and viral production ability is tested for stability over about 20 passages.

Induction of Producer Cell Lines to Generate Virus

Following selection and expansion of the selected clones, the selected clones are induced to produce vector supernatants, and induction may be carried out according to the procedures known to those of ordinary skill in the art. In order to generate the lentiviral vectors produced by induced stable producer lines, the culture supernatant is harvested, in some embodiments, every day for up to 7 days. This production protocol can be easily utilized to produce a variety of test vectors at small scale. The repeated virus harvesting protocol can also increase the final yield of viral vectors. However, the daily harvest and media exchange is often not economical, and as an alternative to the of daily harvest, a new two-day harvest protocol has been devised. This new viral vector production protocol, described below, allows the same amount of viral vectors to be generated with less culture media consumptions.

Figure 19:
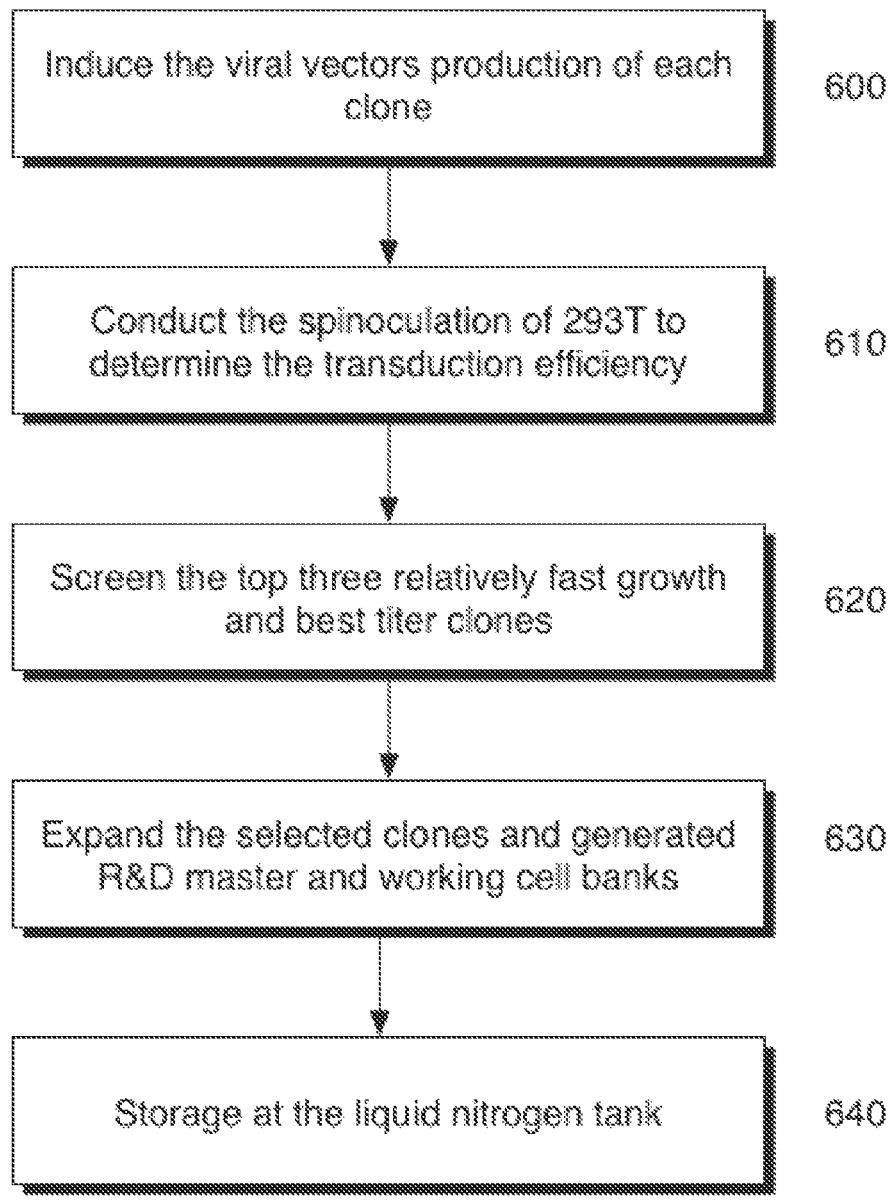
FIG. 19 is a flowchart illustrating a method of evaluating viral production.

FIG. 19 further illustrates the process of induction and evaluation. At step 600, the viral vectors are induced and then the spinoculation of 293T is conducted to determine transduction efficiency (step 610). The top three clones are screened (step 620) and expanded (step 630). The clones are then stored (e.g. under liquid nitrogen) (step 640).

Harvest Every Two Days

Applicants have unexpectedly discovered that a two-day harvest allows for the generation of about the same amount of viral vectors as with a more traditional daily harvest, while also providing the benefit of requiring less culture medium.

In one embodiment is a first method of generating viral vectors from a two-day harvest according to the present invention, the first method comprising the following steps:

(1) Remove the old culture medium of the producer lines culture dish as completely as possible and wash the cells with 1×PBS.

(2) Add TrypLE™ Express Enzyme (1×) to the culture dish (available from ThermoFisher Scientific).

(3) Place in 37° C. incubator for 2 minutes.

(4) Wash out the cells by adding D10 medium (no drug) and dissociate cell clusters into single cells by pipetting up and down (D10 media: Dulbecco's Modified Eagle Medium with high glucose, GlutaMAX™ Supplement and 10% (w/v) FBS and 1% (w/v) Pen/Strep).

(5) Centrifuge cells for 5 minutes at 4° C. at 1200 rpm.

(6) Aspirate medium and gently suspend pellet in fresh D10 medium (no drug).

(7) Seed the cells about 95% confluent at culture dish (Roughly by plating 4×106 Cells/6-mm culture dish, Vectors Induction).

(8) The seeded cells were supplemented with fresh, pre-warm D10 medium after 24 hr (Day 1 post-induction).

(9) Viral vectors can be first time harvested from the cells 48 hours after the first time media change (Day 3 post-induction).

(10) Add the fresh, pre-warm medium to the culture dish.

(11) Conduct the second time viral vector harvested 48 hours after the second time medium change (Day 5 post-induction).

(12) Add the fresh, pre-warm medium to the culture dish.

(13) Conduct the third time viral vector harvested 48 hours after the third time medium change (Day 7 post-induction).

Applicants have found that the viral titer can be yielded at second time viral vectors collection at Day 4 and Day 5 post-induction, as compared with more traditional methods where viral vectors could be collected seven days post induction.

In another embodiment is a second method of generating viral vectors from a two-day harvest according to the present invention, the first method comprising the following steps:

(1) Remove the media of the producer lines culture dish as completely as possible and wash the cells with 1×PBS.

(2) Gently Pipette 1× TrypLE Express onto the washed cell monolayer using 3 mL for 100 mm culture dish.

(3) Rotate flask to cover the monolayer with TrypLE Express.

(4) Return flask to the incubator and leave for 2 minutes.

(5) Gently tapped side of the flasks to release any remaining attached cells.

(6) Re-suspend the cells in 2 mL of the fresh D10 media (no antibiotics) and transfer to a 15 mL conical centrifuge Tube.

(7) Centrifuge cells for 5 minutes at 1200 rpm.

(8) Aspirate media and gently suspend pellet in 5 mL fresh D10 culture media (no antibiotics)

(9) Determine the cell counts by TC10™ Automated Cell Counter

(10) Seed the cells >95% confluent at culture dish (by plating 4×106 Live Cells in 60-mm culture dish)

(11) The seeded cells were supplemented with fresh, warm-up D10 media daily (Every 24 hours).

Applicants have discovered that viral vectors could be harvested from the cells 48 hours post induction and that the highest viral titer could be yielded at 72 hours after induction. Applicants have again unexpectedly discovered that viral vectors could be harvested from days 2-4 post induction.

In some embodiments, the harvested vectors are purified through filtration. In some embodiments, the harvested vectors are characterized by determining viral titer, viral copy per cell genome, and p24 concentration.

Figure 5A:
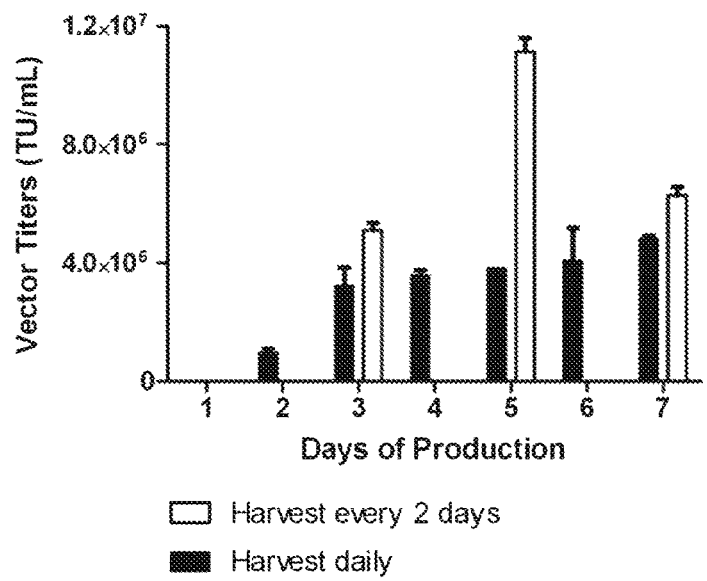
FIG. 5A illustrates the kinetics of lentiviral vector production from stable cell lines. During vector production, the medium was replaced with a fresh medium on a daily basis (■) or every 2 days (□).
Figure 5B:
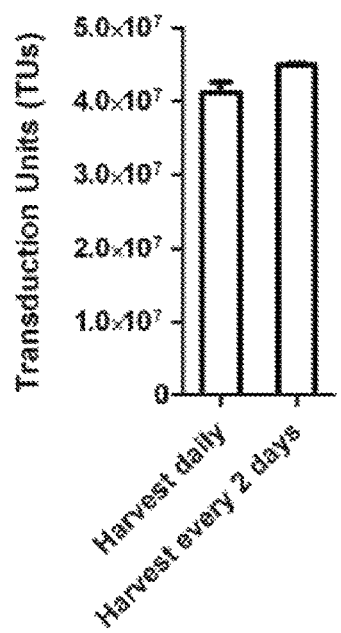
FIG. 5B illustrates the kinetics of lentiviral vector production from stable cell lines. The total amount of LVs in the harvested medium was titrated on 293T cells. The data shown are the mean values±SD (N=2). TUs, transduction units.

Daily comparison of daily harvesting versus two-day harvesting is illustrated in FIG. 5.

Example 1—Detailed Comparison of Self-Inactivating Lentiviral Vectors Produced by Transient Transfection and Vectors Produced by the Disclosed Stable Cell Line Method The methods described herein were used to generate a stable cell line for the production of LVsh5/C46, a self-inactivating lentiviral vector (SIN-LV) encoding a short hairpin RNA (shRNA) for down-regulation of the HIV-1 co-receptor CCR5, in combination with the HIV-1 fusion inhibitor, C46. This LV, produced by transient transfection, is currently being evaluated in clinical trials in HIV-infected individuals. Here we conducted a comparative analysis of LVsh5/C46 produced by transient transfection and LVsh5/C46 produced using the methods described herein to support the application of this system for clinical manufacturing of LVsh5/C46 and other SIN-LVs.

Lentiviral vectors (LVs) were produced by calcium phosphate transfection in 293T cells using the 4-plasmid system (one transfer vector, two packaging vectors, and one envelope vector). Virus-containing media (VCM) was harvested 48 h post-transfection and concentrated by ultracentrifugation through a 20% sucrose cushion.

Figure 9:
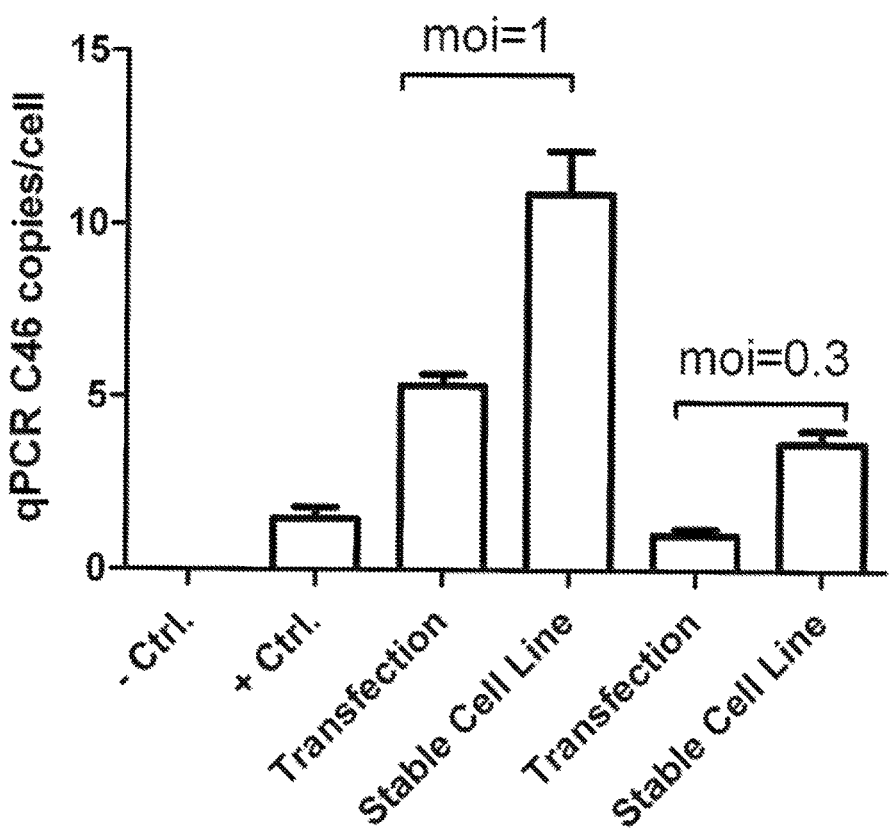
FIG. 9 illustrates the quantification of lentiviral vector copy numbers in the infected cells. C46 qPCR was used to determine the vector copy number per host genome after transduction at two doses (MOI=1 or 0.3).

For cell line production, producer cells were induced in media without doxycycline (Dox), and the VCM was harvested at 72 h and similarly concentrated by ultracentrifugation. With reference to Table 1 and FIGS. 8 and 9, LVs produced by each method were compared based on particle titer and using three independent assays for gene transduction potency on 293T and the TF-1a T cell line. These included FACS assays for cell surface C46 expression and shRNA-mediated knockdown of CCR5 expression, as well as a qPCR assay for vector copy number (VCN) per host cell genome. For all assays, titer was determined over a range of vector dilutions to define a linear relationship. The qPCR assay utilized genomic DNA extracted from transduced cells, and detect the C46 transgene and a sequence from the endogenous β-globin gene. As such, C46 VCN could be normalized to cellular genome.

TABLE 1

Stable vs. Transient viral vector production.

| VCM[2] | Method | Titer 293T (TU/mL) | Titer TF-1a (TU/mL) | p24 (ng/mL) |
|---|---|---|---|---|
| LVsh5/C46 | Transient Transfection | $2.78 \times 10^8$ | $2.64 \times 10^8$ | 5250 |
| TL20sh5/C46 | Stable Producer Cell | $1.40 \times 10^8$ | $1.46 \times 10^8$ | 13430 |

Figure 10:
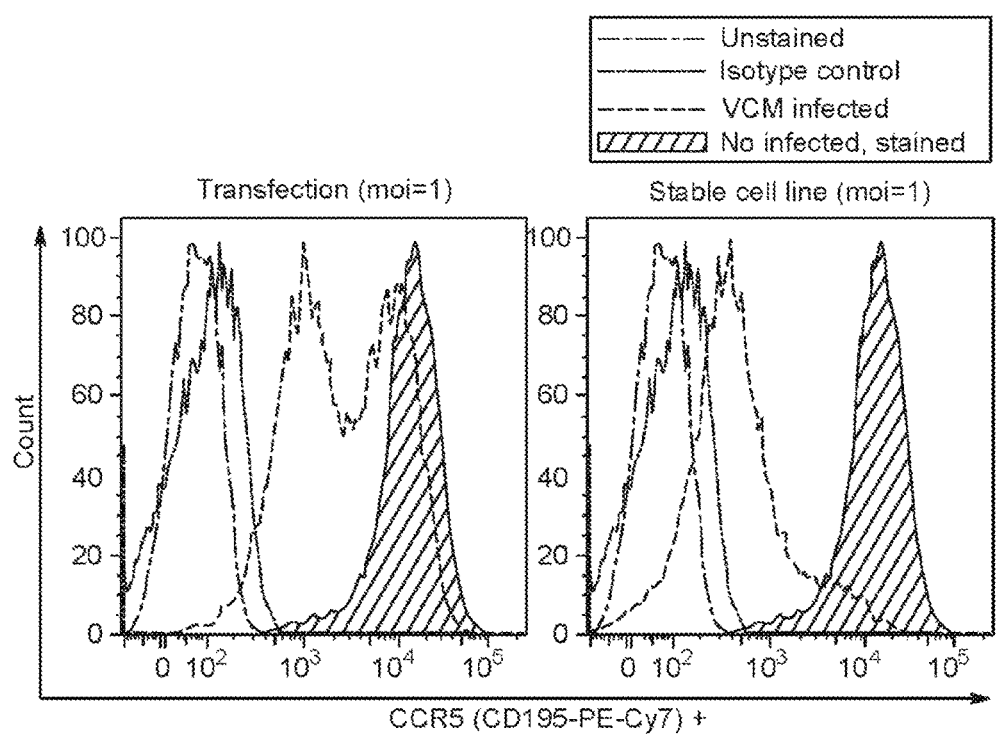
FIG. 10—Ghost-CCR5 cells were transduced with LVsh5/C46 vectors. The decreased level of CCR5 expression was measured by FACS.

1. Abbreviation: TU, Transduction Unit; VCM, virus-containing medium
[2]VCM were concentrated 100-fold through a 20% sucrose cushion by ultracentrifugation A higher concentration of p24 was observed in VCM produced by producer cell lines relative to transient transfection method. However, yield and potency of LVsh5/C46 produced using the two different systems was similar. Vectors were first evaluated for C46 titer by FACS using equal volumes of VCM. While vector produced by transient transfection had a modestly increased titer, when C46 titers were normalized and vector preparations were assed for gene transduction using the qPCR assay or via functional knock-down of CCR5, vector produced by the stable producer cell lines showed greater potency (see Table 2). Down-regulation of CCR5 expression and genomic C46 transgene (VCN) were each significantly higher in the target cells treated with LVsh5/C46 produced by the methods disclosed herein than treated with vector produced by transient transfection (see Table 3 and FIG. 10).

TABLE 2

Analysis of C46 by qPCR in transduced cells

| Condition | MOI[3] | C46 copies/cells |
|---|---|---|
| no virus, negative ctrl. | — | ND |
| TF-1a[2], positive ctrl. | — | 1.36 ± 0.58 |
| Transient Transfection | 1 | 5.34 ± 0.55 |
| Stable Producer Line | 1 | 10.7 ± 2.17 |
| Transient Transfection | 0.3 | 1.01 ± 0.30 |
| Stable Producer Line | 0.3 | 3.67 ± 0.66 |

1. Abbreviation: ND, Not Detected; MOI, Multiplicity of Infection
[2]LVsh5/C46 single copy cell line
[3]MOI based on C46 transduction titer

TABLE 3

Analysis of C46 by qPCR in transduced cells

| Condition | MOI[3] | C46 copies/cells |
|---|---|---|
| no virus, negative ctrl. | — | ND |
| TF-1a[2], positive ctrl. | — | 1.36 ± 0.58 |
| Transient Transfection | 1 | 5.34 ± 0.55 |
| Stable Producer Line | 1 | 10.7 ± 2.17 |
| Transient Transfection | 0.3 | 1.01 ± 0.30 |
| Stable Producer Line | 0.3 | 3.67 ± 0.66 |

1. Abbreviation: ND, Not Detected; MOI, Multiplicity of Infection
[2]LVsh5/C46 single copy cell line
[3]MOI based on C46 transduction titer Based on three independent assays, we demonstrate that the methods described herein provide a stable LV production system is capable of generating similar quality and quantity of SIN-LVs compare to transient transfection method. The higher CCR5 down-regulation efficacy and C46 VCN in transduced cells (normalized to C46 titer) indicate that LVsh5/C46 produced by producer cells has better potency than those vectors generated using the conventional 4-plasmid transient transfection. By removing the tedious transient transfection step, without wishing to be bound by any particular theory, it is believed that this production system can be easily adapted to cGMP conditions for the manufacture of clinical grade materials for use in humans.

Example 2—Development and Characterization of GPRG-Based Producer Cell Lines for the Bio-Production of Lentiviral Vectors for HIV Gene Therapy The GPRG cell line system has previously been established for the clinical production of self-inactivating lentiviral vectors (SIN-LVs). Here we sought to establish producer cell lines based on GPRG for the production of LVsh5/C46, a SIN-LV currently being assessed in the clinic for treatment of HIV-infected individuals. This vector encodes two viral entry inhibitors; sh5, a short hairpin RNA to the HIV co-receptor CCR5, and C46, a viral fusion inhibitor. We also sought to define the stability of GPRG packaging cell line, the GRPG-based LVsh5/C46 producer cell line, and LVsh5/C46 production following tetracycline induction as required for regulatory filling and clinical application of the GPRG system for bio-production of LVsh5/C46.

Figure 3:
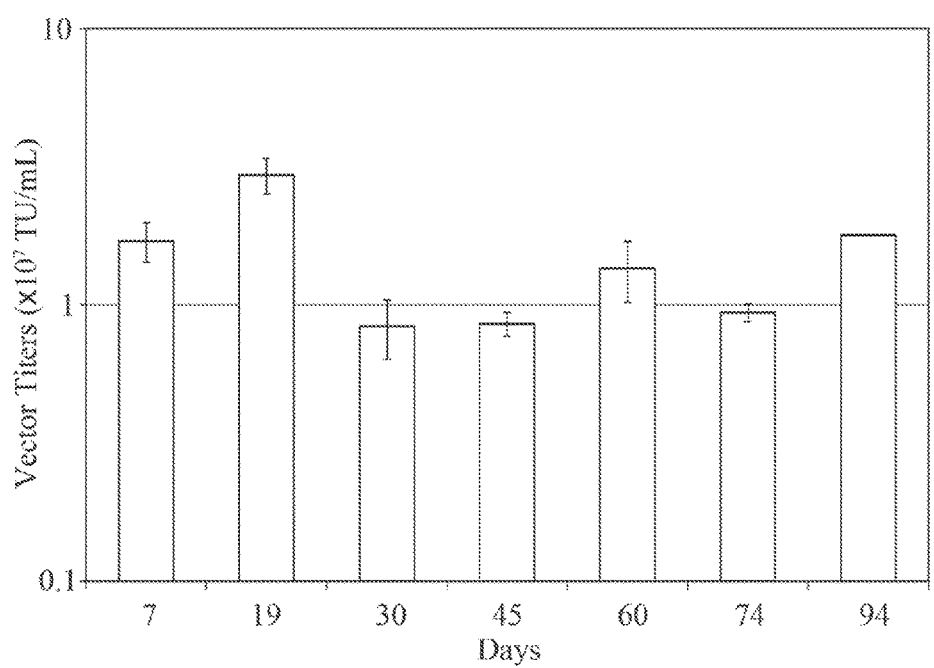
FIG. 3 illustrates the assessment of producer cell line stability for two different cell line MWCBs over a three-month period of continuous passage. At regular intervals, LV was induced by tetracycline (TET) removal and VCM was assessed for LV titer by gene transduction assay. Both cell lines were stable and able to produce LV in excess of 1e6/ml over the three-month period and for in excess of about 25 passages.
Figure 4:
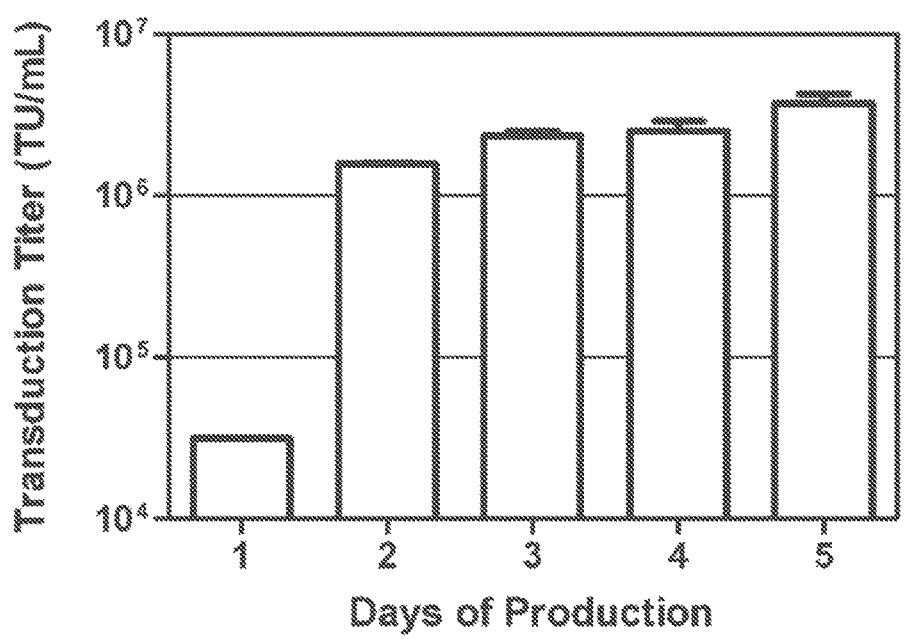
FIG. 4 illustrates the kinetics of lentiviral vector production following induction by removal of TET. Vector titer was assessed in VCM by gene transduction assay. In all instances, GPRG-based stable producer cell lines have been able to maintain LV production at levels above 1e6 TU/ml (unconcentrated) for at least 5 days following induction.

GPRG cells were cultured in D10 media with doxycycline (Dox) and puromycin (Puro). To generate LVsh5/C46 producer cells, GPRG cells were transfected with the transfer plasmid TL20-LVsh5/C46 and a Zeocin-resistance plasmid as a concatemeric array. Individual clones were evaluated for their ability to produce LVsh5/C46 vector and maintained in D10 media with Dox, Puro, and Zeocin. To assess the stability of the parental GPRG cell line for LV production, GPRG cells were transfected with transfer vector every 10 passages over a 3-month period (50+ total passages) (see FIGS. 3A and 3B). Virus-containing media (VCM) was harvested 48 h post-transfection and vector titer was assessed by complementary gene transduction assays. To assess the stability of LV production from the stable producer cell clones, cells were induced in D10 media without Dox. VCM was harvested 72 h after induction and titer was similarly assessed over a range of vector dilutions. To analyze the stability of VSV-G expression following induction after long-term passage, GPRG cells were induced by Dox withdraw and then stained using a biotin-conjugated anti-VSV-G antibody, followed by a secondary staining with Streptavidin-Phycoerythrin.

Figure 6A:
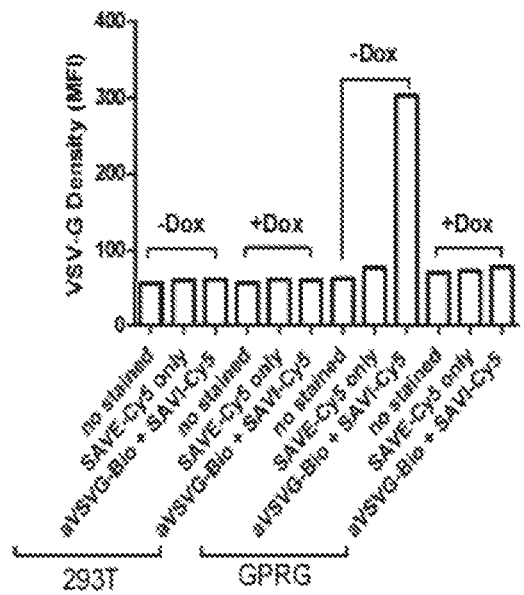
FIG. 6A illustrates GPRG and 293T cells were induced in medium without doxycycline (Dox). The induced cells were stained by anti-VSVG antibodies to detect the VSVG expression and measured by flow cytometry.
Figure 6B:
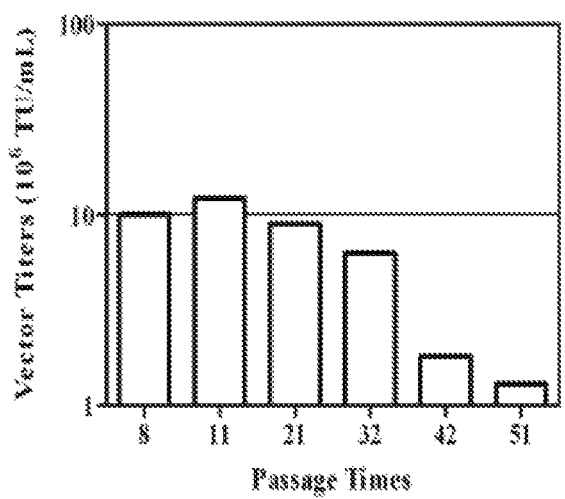
FIG. 6B illustrates the ability of the GPRG to produce LV was assessed after prolonged culture.

GPRG cells demonstrate stringent tetracycline-regulated expression of VSV-G. This packaging cell line was able to produce up to 107 LV transduction units (TU)/mL after transfection with the LV transfer vector and maintained high-level LV production for more than 50 passages in continuous culture (see FIGS. 6A and 6B). By utilizing concatemeric array transfection, we demonstrate efficient construction of a producer cell line based on GPRG for the production of LVsh5C46. This cell line consistently generated titers above 106 TU/mL. Further increases in titer could be achieved by recloning and selection of secondary producer cell lines. Titers peaked 2 to 5 days post-induction. We also showed that the established stable producer cell lines could routinely maintain LVsh5/C46 production with titers exceeding 106 TU/mL during continuous culture exceeding 25 passages.

Figure 7:
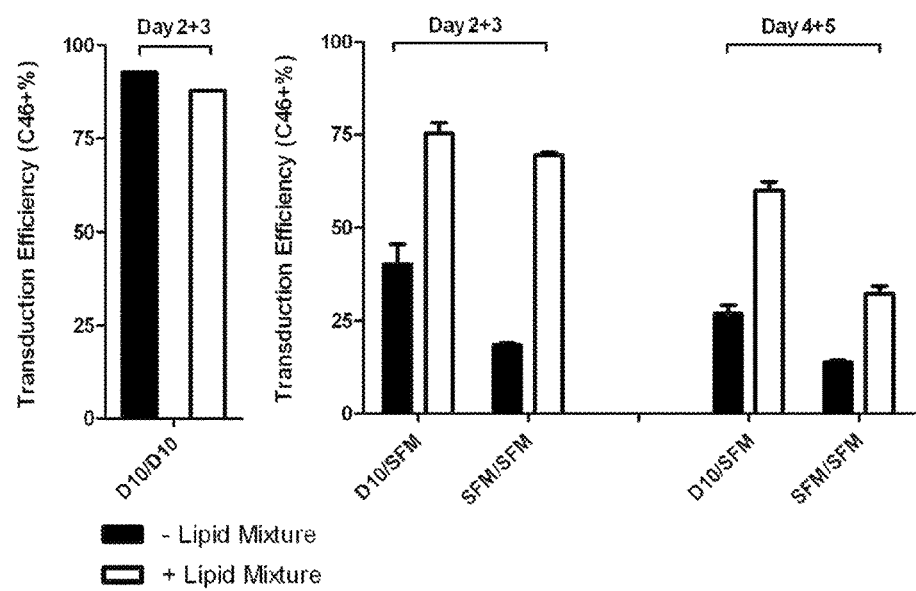
FIG. 7 illustrates lentiviral production in different culture conditions. (A) Cultured/Produced in serum-containing medium. (B, Left) Cultured in serum-containing/Produced in serum-free medium; (B, Right) Cultured/Produced in serum-free medium. D10: 500 mL DMEM/GlutaMAX™; 50 mL FBS (10% w/v); 5 mL Pen/Strep; SFM: serum-free medium.

The GPRG cell line efficiently expressed VSV-G on cell surfaces upon the removal of Dox. It could also generate high titers LVs after transfection of transfer vector plasmids. Moreover, this cell line allowed the derivation of high-titer producer cell lines for SIN-LVs. Producer cell lines demonstrated stable vector production during prolonged culture, and evaluation of the adaptability to adapt vector production to serum-free and suspension culture systems has been explored (see FIGS. 7A and 7B).

Example 3—Protocol for the Generation of a Concatemeric Array

Step 1

Prepare 500 mL of 1×TAE running buffer by combining 490 mL of Deionized water with 10 mL 50×TAE ((Tris-acetate-EDTA) buffer).

Make the 1% agarose gel by adding 1 g of Agarose and 100 mL of 1×TAE buffer (Add 2 mL 50×TAE with 98 mL Autoclaved water) into a beaker and microwaving the mixture until there is no solid particles or bubbles (about 2.5 minutes).

Allow the mixture to cool for 3 minutes.

Add 10 µL of GelRed™ into the Agarose gel mixture and stir (available from Biotium).

Assemble the gel caster and gel comb. Pour the mixture into the gel mold and let it cool for 30 minutes (capacity: 60 µL for big comb)

Once the gel is cooled, fill the box with 1×TAE buffer until the gel is completely submerged.

Prepare the digest reaction mixture at room temperature to linearize the DNA

Digest 25 µg of the vector plasmid with the restriction enzyme SfiI. In a separate reaction, digest the resistance cassette plasmid PGK-ble with PflMI (10 µg is more than enough).

| Component | The ble marker | Vector |
|---|---|---|
| DNA Name | PGK-ble | |
| 10 FastDigest Green Buffer | 5 µL | 10 µL |
| Plasmid DNA | 10 µg | 25 µg |
| FastDigest Enzyme 1: PflMI | 5 µL | 0 µL |
| FastDigest Enzyme 2: SfiI | 0 µL | 5 µL |
| Water, nuclease-free | To 50 | To 100 |
| Total Volume | 50 µL | 100 µL |

Mix gently and incubate at 37° C. in a heat for 15 min.

Add 10 µL of GeneRuler 1 kb plus DNA ladder mixture (2 µL DNA ladder+8 µL nuclease-free water) and 50 µL of sample mix into the available slots.

Turn on the electrophoresis machine and run with the voltage of 150 V for 1 hour.

Transfer the gel into the UVP PhotoDoc-It Imaging system, and obtain the image of the result.

Download the gel pictures from the Eye-Fi website.

Determine the DNA concentration of each sample using the NanoDrop 2000 Spectrophotometer.

Step 2

Cut DNA bands out of the Agarose gel.

Add 3 volumes of Buffer QG to 1 volume of gel (Generally add 500 µL QG).

Incubate at 50° C. for 10 minutes after the gel slice has dissolved completely.

Apply the sample to the QIAquick column, and centrifuge for 1 min at 17,900 rpm (available from Qiagen).

Discard flow-through and place QIAquick column back in the same collection tube.

Add 0.5 ml of Buffer QG to QIAquick column and centrifuge for 1 min.

Add 0.75 ml of Buffer PE to QIAquick column and centrifuge for 1 min.

Discard the flow-through and centrifuge the QIAquick column for an additional 1 min at 17,900 rpm.

Place QIAquick column into a clean 1.5 ml microcentrifuge tube.

To elute DNA, add 35 µL of Buffer EB to the center of the QIAquick membrane and centrifuge the column for 1 min at 17,900 rpm (Buffer EB is 10 mM Tris-cl, pH 8.5).

Measure the DNA fragments concentration using the NanoDrop 2000 Spectrophotometer (Table 1; Using EB buffer for the Blank measurement)

Step 3

Set up the ligation reaction in a 1.7 mL Eppendorf microcentrifuge tube on ice.

Use the pre-constructed spreadsheet (Concatemeric Ligations.xlsx) to calculate the volumes of each fragment that needs to be mixed to create about a 25:1 molar ratio of vector to PGK-ble.

Maximize the volume of fragments in the ligation reaction and maintain the desired molar ratio.

The T4 DNA Ligase Buffer should be thawed and re-suspended at room temperature (T4 DNA Ligase Buffer comprises the following components: 50 mM Tris-HCl, 10 mM MgCl2, 1 mM ATP, 10 mM DTT, pH 7.5).

Pipette the ligation reaction. In the above example, we used the 90 µL DNA mixture by adding 10 µL of 10× ligation buffer (NEB Quick Ligation kit), and 0.5 µL of Ligase enzyme (available from New England BioLabs).

Prepare the following reaction mixture containing at room temperature:

| Component | Vector |
|---|---|
| The vector fragment | |
| The ble-resistant fragment | |
| 10 × T4 DNA Ligase Buffer | 10 |
| T4 DNA Ligase | 0.5 |
| Water, nuclease-free | To 90 |
| Total Volume | 90 |

Mix gently by pipetting up and down.

Incubate at room temperature for overnight

Step 4

The concatemeric array was harvested and purified prior to transfection into GPRG cells by the silica-based membrane (DNeasy Blood & Tissue Kit).

Pipet the concatemeric array mixture into the DNeasy Mini spin column placed in a 2 ml collection tube.

Centrifuge at 8000×g for 1 min. Discard flow-through and collection tube.

Place the DNeasy Mini spin column in a new 2 ml collection tube (provided) (available from Qiagen).

Add 500 µLBuffer AW1, and centrifuge for 1 min at 8000×g.

Discard flow-through and collection tube

Place the DNeasy Mini spin column in a new 2 ml collection tube (provided)

Add 500 µL Buffer AW2, and centrifuge for 3 min at 20,000×g to dry the DNeasy membrane.

Discard flow-through and collection tube.

Place the DNeasy Mini spin column in a clean 1.7 ml Eppendorf microcentrifuge tube Add 200 µL Buffer AE directly onto the DNeasy membrane.

Incubate at room temperature for 4 min

Centrifuge for 1 min at 8000×g to elute the DNA mixtures.

Repeat elution once

Measure the concatemeric DNA concentration by the NanoDrop Lite Spectrophotometer Example 4—Protocol for Generating Producer Cell Lines Using a Concatemeric Array Passage the cells at least 4 times after thawing before using them in the viral vector production.

Ensure that cells are healthy and greater than 95% viable before vectors induction using Trypan Blue method (Trypan Blue is commonly used in dye exclusion procedures for viable cell counting. This method is based on the principle that live (viable) cells do not take up certain dyes, whereas dead (non-viable) cells do. Staining facilitates the visualization of cell morphology).

Culture the desired quantity of GPRG cells

Subculture the cells at least two times daily passage before seed the cells.

The first day, remove the medium of the GPRG cell lines culture dish and wash the cells with 1×PBS.

Gently Pipette 1×TrypLE Express onto the washed cell monolayer using 3 ml for T75 flask or 1 mL for T25 Flask.

Rotate flask to cover the monolayer with TrypLE Express.

Return flask to the incubator and leave for 2 minutes.

Gently tapped side of the flasks to release any remaining attached cells.

Re-suspend the cells in 2 mL of the fresh D10 medium and transfer to a 15 mL conical centrifuge tube.

Centrifuge cells for 5 minutes at 1200 rpm.

Aspirate medium and gently suspend pellet in 5 mL fresh D10 culture medium with Doxycycline (1 ng/mL)

Determine the cell counts by TC10™ Automated Cell Counter (Table 5)

Seed the cells 20-24 hours before the transfection at 80% confluent at culture dish (by plating 3.2×106 Live Cells in 60-mm culture dish with Doxycycline; Table 9)

Prepare the concatemeric arrays formation (see, for example, Example 3).

The second day, allow CalPhos™ Mammalian Transfection Kit to come to room temperature prior to the transfection (Table 7) (available From ClonTech).

Purify the concatemeric DNA and measure the concentration (the concatemeric array may be purified according to the methods described herein)

Prepare the transfection plasmid DNA table (Table 8; 4 mL, 60 mm culture dish).

For each transfection, prepare Solution A and Solution B in the separate 15 mL conical centrifuge tube Bubbling Solution B (2×HBS) by Pipette-aids and add the Solution A (DNA mixture) drop by drop.

Incubate the transfection solution at room temperature for 15 min

Gently add the transfection solution to the culture dish.

Gently move plates back and forth to distribute transfection solution evenly.

Incubate plates at 37° C. for 4 hours in a CO2 incubator.

Warm-up 5 mL fresh D10 media per 60 mm culture dish in a 37° C. CO2 incubator

After 4 hours wash with 1 mL pre-warmed D10 and change with 4 mL pre-warmed fresh D10 medium Incubate at the 5% CO2 37° C. incubator 48 hours after concatemer transfection, harvest the transfected GPRG cells (Perform the Subculturing Cells).

Re-plate the cells in the T150 flask or the 30 mL, 150 mm culture dish with fresh D10 media containing Zeocin (50 ug/ml) and Doxycycline (1 ng/mL)

Feed the cells with selective medium (Zeocin, 50 ug/ml) with Doxycycline (1 ng/mL) every 3-4 days until the cell foci are identified (usually observed within 1-2 weeks)

Example 5—Description of Cell Lines and Sequences Used to Generate the GPRG Packaging Cell Line HEK-293T/17 are a sub-clone of HEK-293T. These cells stably express SV-40 T antigen, and a particular clone was selected specifically for its high transfectability. A master cell bank based on HEK-293T/17 was generated (HEK-293T/17 MCB).

SFG-IC-HIVgp-Ppac2 is a gamma retroviral vector that expresses codon-optimized HIV gagpol under control of the CMV promoter, with puromycin resistance. The plasmid (pSFG-IC-HIVgp-Ppac2) that was used to make this vector was constructed using the following components:

(1) pSFG tcLuc ECT3 is a derivative of a retrovirus vector backbone plasmid (SFG), adapted for regulated gene expression using the tetracycline-regulated promoter system (Lindemann, D., Patriquin, E., Feng, S., & Mulligan, R. C. Versatile retrovirus vector systems for regulated gene expression in vitro and in vivo. Mol. Med. 3, 466-476 (1997));

(2) CMV enhancer/promoter driven codon optimized HIV NL4-3 gagpol gene;

(3) PGK promoter driven puromycin resistance gene derived from pMSCVpac (Hawley, R. G., Lieu, F. H., Fong, A. Z., & Hawley, T. S. Versatile retroviral vectors for potential use in gene therapy. Gene Ther. 1, 136-138 (1994)).

Infection of the HEK-293T/17 MCB with the SFG-IC-HIVgp-Ppac2 retroviral vector produced the GP cell line.

SFG-tc-revco is a gamma retroviral vector that expresses codon-optimized HIV rev under control of the tetracycline responsive promoter. The plasmid used to produce this vector (pSFG-tc-revco) was constructed using the following components:

(1) The HIV rev gene based on the NL4-3 strain sequence as above, and (2) pSFG tcLuc ECT3 (described above)

SFG-tTA is a gamma retroviral vector that expresses the chimeric transcriptional transactivator under control of the retroviral LTR (Lindemann, D., Patriquin, E., Feng, S., and Mulligan, R. C. Versatile retrovirus vector systems for regulated gene expression in vitro and in vivo. Mol. Med. 3, 466-476 (1997)). It is based on the SFG retroviral vector, an incorporates a Tet promoter element from plasmid pUHD15-1 (Gossen M, and Bujard, H. (1992) PNAS 89 12:5547-5551).

Infection of the GP cell line with SFG-tc-revco and SFG-tTA produced the GPR cell line SFG-tc-VSVG is a gamma retroviral vector that expresses VSV glycoprotein G under control of the tetracycline-regulated promoter. The plasmid used to make this vector (pSFG-tc-VSVG) was generated using the same pSFGtcLucECT3 backbone as the other vectors, and plasmid pMD.G as a source of the VSVG envelope protein (see Ory, D. S., Neugeboren, B. A., and Mulligan, R. C. A stable human-derived packaging cell line for production of high titer retrovirus/vesicular stomatitis virus G pseudotypes. Proc. Natl. Acad. Sci. U.S.A 93, 11400-11406 (1996) and Rose, J. K. & Gallione, C. (1981) J. Virol. 39, 519-528).

Infection of the GPR cell line with SFG-tc-VSVG produced the GPRG cell line.

Infection of GPR cell line with Retro-SVGmu to generate GPRS cell line is described by Lee, Chi-Lin et al. "Construction of Stable Producer Cells to Make High-Titer Lentiviral Vectors for Dendritic Cell-Based Vaccination." Biotechnology and Bioengineering 109.6 (2012): 1551-1560. PMC. Web. 14 Apr. 2016.

Example 6—Concatemeric Array Purification

The concatemer was harvested and purified prior to transfection into GPRG cells by the silica-based membrane (DNeasy Blood & Tissue Kit).

Pipet the concatemeric array mixture into the DNeasy Mini spin column placed in a 2 mL collection tube.

Centrifuge at 6000×g for 1 min. Discard flow-through and collection tube

Place the DNeasy Mini spin column in a new 2 mL collection tube (provided)

Add 500 µLBuffer AW1, and centrifuge for 1 min at 6000×g.

Discard flow-through and collection tube

Place the DNeasy Mini spin column in a new 2 ml collection tube (provided)

Add 500 µL Buffer AW2, and centrifuge for 3 min at 20,000×g to dry the DNeasy membrane.

Discard flow-through and collection tube.

Place the DNeasy Mini spin column in a clean 1.7 mL Eppendorf microcentrifuge tube Add 200 µL Buffer AE directly onto the DNeasy membrane.

Incubate at room temperature for 4 min

Centrifuge for 1 min at 6000×g to elute the DNA mixtures.

Repeat elution once (add new elution buffer)

Measure the concatemeric DNA concentration by the NanoDrop Lite Spectrophotometer.

Example 7—TL20-UbcGFP & Cal1-WPRE Producer Cell Line

Figure 20A:
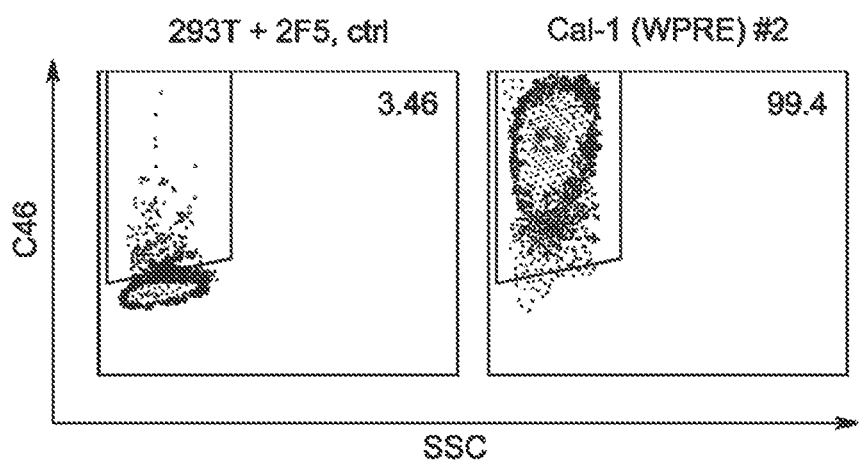
FIGS. 20A, 20B, and 20C, in general, describe producer cells for synthesizing TL20-Cal1-wpre and TL20-Unc-GFP vectors.
Figure 20B:
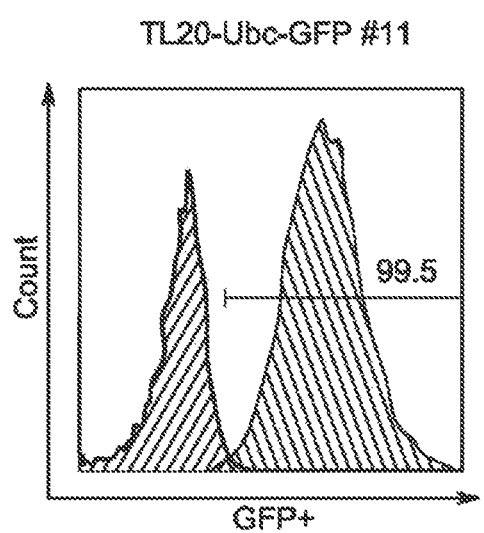
Figure 20C:
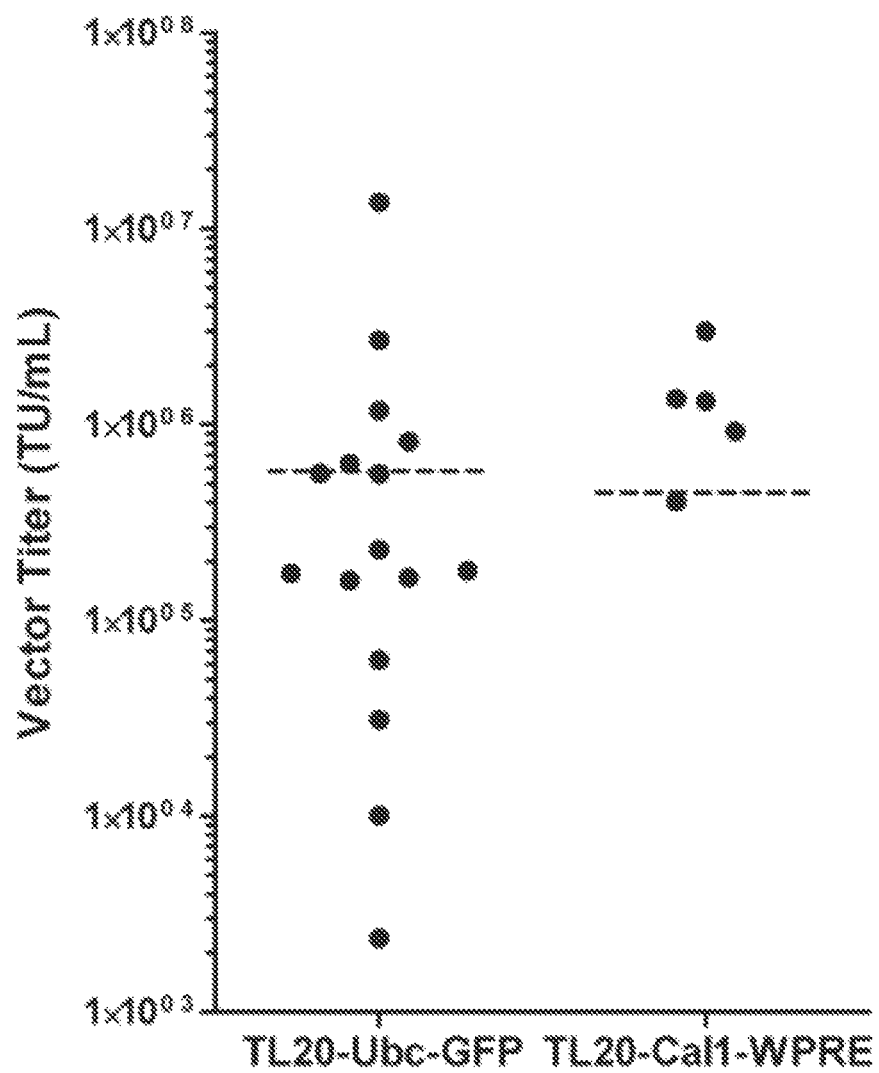

The Table which follows summarizes two producer cell lines that were synthesized according to the methods describes herein. Data relating to the TL20-Cal1-wpre and TL20-Unc-GFP vectors is illustrated further in FIGS. 20A, 20B, and 20C.

| Selection and Screening | TL20c-Ubc-GFP | TL20c-Cal1-WPRE |
|---|---|---|
| Method | Single Cell Sorting[2] | Single Cell Sorting[2] |
| Seed Cell Density | 1 cell/well | 1 cell/well |
| Culture Medium | Conditioned Medium | Conditioned Medium |
| Efficiency of clone formation | 28/96 | 22/96 |
| Complete Expanded | 16 | 17 |
| Evaluated clones | 16 | 5 |
| Polyclonal Vector Production | $5.77 \times 10^5$ TU/mL | $4.50 \times 10^5$ TU/mL |
| The productivity of the best clones | $1.36 \times 10^7$ TU/mL | $3.0 \times 10^6$ TU/mL |

1. Abbreviation: TU, Transduction Unit
[2]Performing single cell sorting by using flow cytometer at USC Flow Cytometry Core Facility
3. Conditioned Media: DMEM w GlutaMax; FBS (10% w/v); Pen/Strep (1% w/v); Doxycycline (1 ng/mL)

ADDITIONAL EMBODIMENTS

Embodiment 1

A recombinant plasmid comprising a nucleotide sequence having at least 90% identity to that of SEQ ID NO: 1.

Embodiment 2

The recombinant plasmid of embodiment 1, wherein the nucleotide sequence has at least 95% identity to that of sequence of SEQ ID NO: 1.

Embodiment 3

A recombinant plasmid comprising the nucleotide sequence of SEQ ID NO: 1.

Embodiment 4

A recombinant plasmid comprising a nucleotide sequence having at least 90% identify to that of SEQ NO: 2.

Embodiment 5

A recombinant plasmid having a sequence that differs by not more than 100 nucleotides from the sequence set forth in SEQ ID NO: 1.

Embodiment 6

The recombinant plasmid of embodiment 5, wherein the sequence differs by not more than 50 nucleotides from the sequence set forth in SEQ ID NO: 1.

Embodiment 7

A recombinant plasmid comprising between about 6500 nucleotides and about 6750 nucleotides, and wherein the plasmid comprises a sequence having at least 90% identity to that of SEQ ID NO: 2.

Embodiment 8

The recombinant plasmid of embodiment 7, wherein the plasmid comprises between about 6600 nucleotides and about 6700 nucleotides.

Embodiment 9

The recombinant plasmid of embodiment 7, wherein the plasmid comprises about 6611 nucleotides.

Embodiment 10

A recombinant plasmid as set forth in FIG. 11 as pUC57-TL20c.

Embodiment 11

A recombinant plasmid comprising a multiple cloning site consisting essentially of BstBI, MluI, NotI, and ClaI restriction endonuclease sites.

Embodiment 12

The recombinant plasmid of embodiment 11, wherein the plasmid further comprises a nucleotide sequence encoding a packaging signal; a nucleotide sequence encoding a central polypurine tract; a nucleotide sequence encoding a Rev response element; and a nucleotide sequence encoding a self-inactivating long terminal repeat.

Embodiment 13

A recombinant plasmid comprising (a) a nucleotide sequence encoding a packaging signal; (b) a nucleotide sequence encoding a central polypurine tract (cPPT); (c) a nucleotide sequence encoding a Rev response element; (d) a nucleotide sequence encoding a self-inactivating long terminal repeat; and (e) a nucleotide sequence encoding a multiple cloning site having restriction sites for the enzymes BstBI, Mlu I, Not I, and Cla I.

Embodiment 14

The recombinant plasmid of embodiment 13, where the nucleotide sequence encoding the packing signal comprises the sequence of SEQ ID NO: 3.

Embodiment 15

The recombinant plasmid of embodiment 13, wherein the nucleotide sequence encoding the central polypurine tract (cPPT) comprises the sequence of SEQ ID NO: 4.

Embodiment 16

The recombinant plasmid of embodiment 13, wherein the nucleotide sequence encoding the Rev response element comprises the sequence of SEQ ID NO: 5.

Embodiment 17

The recombinant plasmid of embodiment 13, wherein the nucleotide sequence encoding the self-inactivating long terminal repeat comprises the sequence of SEQ ID NO: 6.

Embodiment 18

The recombinant plasmid of embodiment 13, wherein the nucleotide sequence encoding the multiple cloning site comprises the sequence of SEQ ID NO: 7.

Embodiment 19

A recombinant plasmid comprising (a) a packaging sequence, the packaging sequence present from about nucleotide 762 to about nucleotide 1104 of a nucleotide sequence of the plasmid; (b) a central polypurine tract, the central polypurine tract present from about nucleotide 1121 to about nucleotide 1597 of the plasmid nucleotide sequence; (c) a Rev response element, the Rev response element present from about nucleotide 1598 to about nucleotide 2366 of the plasmid nucleotide sequence; (d) a self-inactivating long terminal repeat, the self-inactivating long terminal repeat present from about nucleotide 409 to about nucleotide 589 of the plasmid nucleotide sequence; and (e) a multiple cloning site, the multiple cloning site present from about nucleotide 2376 to about nucleotide 2400 of the plasmid nucleotide sequence.

Embodiment 20

The recombinant plasmid of embodiment 19, wherein the plasmid nucleotide sequence comprises a sequence having at least 90% identity to that of SEQ ID NO: 1.

Embodiment 21

The recombinant plasmid of embodiment 19, where a nucleotide sequence encoding the packing signal comprises the sequence of SEQ ID NO: 3.

Embodiment 22

The recombinant plasmid of embodiment 19, wherein a nucleotide sequence encoding the central polypurine tract (cPPT) comprises the sequence of SEQ ID NO: 4.

Embodiment 23

The recombinant plasmid of embodiment 19, wherein a nucleotide sequence encoding the Rev response element comprises the sequence of SEQ ID NO: 5.

Embodiment 24

The recombinant plasmid of embodiment 19, wherein a nucleotide sequence encoding the self-inactivating long terminal repeat comprises the sequence of SEQ ID NO: 6.

Embodiment 25

The recombinant plasmid of embodiment 19, wherein a nucleotide sequence encoding the multiple cloning site comprises the sequence of SEQ ID NO: 7.

Embodiment 26

A recombinant plasmid comprising a multiple cloning site comprising BstBI, MluI, NotI, and ClaI restriction endonuclease sites, and wherein the plasmid comprises a nucleotide sequence having at least 80% identify to that of SEQ ID NO:1.

Embodiment 27

A recombinant plasmid comprising a nucleotide sequence encoding a vector cassette having at least 95% identity to that of SEQ ID NO: 2, and wherein the vector cassette is flanked by at least two restriction endonuclease sites, the at least two restriction endonuclease sites independently selected from the group consisting of sfiI and Bsu36I.

Embodiment 28

A recombinant plasmid comprising a nucleotide sequence encoding a vector cassette having at least 90% identity to that of SEQ ID NO: 2, the vector cassette comprising a multiple cloning site having BstBI, MluI, NotI, and ClaI restriction endonuclease sites, wherein the plasmid further comprises a tetracycline repressible promoter upstream of the vector cassette.

Embodiment 29

A cell comprising the plasmid of any of embodiments 1 to 28.

Embodiment 30

A kit comprising the plasmid of any of embodiments 1 to 28 and a bleomycin resistance (ble) cassette.

Embodiment 31

A method of producing a stable producer cell line comprising: (a) synthesizing a lentiviral vector by cloning one or more genes into the plasmid of any of embodiments 1 to 28; (b) generating DNA fragments from the synthesized lentiviral vector; (c) forming a concatemeric array from the generated DNA fragments from the synthesized lentiviral vector and from DNA fragments from an antibiotic resistance cassette plasmid; (d) transfecting a GPR, GPRG, GPRT, GPRGT, GPRT-G packing cell line or a derivative thereof with the formed concatemeric array; and (e) isolating the stable producer cell line.

Embodiment 32

A method of producing a stable producer cell line comprising: (a) synthesizing a lentiviral vector which encodes a short hairpin RNA for down-regulation of an HIV-1 co-receptor and which encodes an HIV-1 fusion inhibitor, the lentiviral vector synthesized by cloning cDNA encoding both the short hairpin RNA and the fusion inhibitor into the plasmid of any of embodiments 1 to 28; (b) generating DNA fragments from the synthesized lentiviral vector; (c) forming a concatemeric array from the generated DNA fragments from the synthesized lentiviral vector and from DNA fragments from an antibiotic resistance cassette plasmid; (d) transfecting a GPR, GPRG, GPRT, GPRGT, GPRT-G packing cell line or a derivative thereof with the formed concatemeric array; and (e) isolating the stable producer cell line.

Embodiment 33

A method of harvesting vector supernatant from a stable producer cell line, wherein the vector supernatant is harvested every about 40 hours to about 56 hours.

Embodiment 34

A method of harvesting vector supernatant comprising LVsh5/C46 lentiviral vector, wherein the vector supernatant is harvested every about 40 hours to about 56 hours.

Embodiment 35

A stable producer cell line suitable for producing LVsh5/C46.

Embodiment 36

The stable producer cell line of embodiment 35, wherein the stable producer cell line is based on the GPRG packaging cell line.

Embodiment 37

The stable producer cell line of embodiment 35, wherein the stable producer cell line is based on the GPRT packaging cell line.

Embodiment 38

The stable producer cell line of embodiment 35, wherein the stable producer cell line is based on the GPR packaging cell line.

Embodiment 39

A stable producer cell line suitable for producing a self-inactivating lentiviral vector, the lentiviral vector comprising a nucleotide sequence having at least 90% identity to that of SEQ ID NO: 8.

Embodiment 40

The stable producer cell line of embodiment 39, wherein the stable producer cell line is based on the GPRG packaging cell line.

Embodiment 41

The stable producer cell line of embodiment 39, wherein the stable producer cell line is based on the GPRT packaging cell line.

Embodiment 42

The stable producer cell line of embodiment 39, wherein the stable producer cell line is based on the GPR packaging cell line.

Embodiment 43

A concatemeric array comprising DNA fragments from a first plasmid and a second plasmid; the first plasmid derived from pUC57-TL20c; the second plasmid comprising a bleomycin antibiotic resistance cassette; wherein a ratio of the DNA fragments from the first plasmid to the second plasmid ranges from about 25:1 to about 1:25.

Embodiment 44

A stable producer cell line, the stable producer cell line generated by transfecting a packaging cell line selected from the group consisting of a GPR, GPRG, GPRT, GPRGT and GPRT-G packing cell line or a derivative thereof with the concatemeric array of embodiment 43.

Embodiment 45

The stable producer cell line of embodiment 44, wherein the stable producer cell line produces LVsh5/C46.

Embodiment 46

The stable producer cell line of embodiment 45, wherein the LVsh5/C46 is capable of being harvested every about 40 hours to about 56 hours.

Embodiment 47

An isolated vector having the plasmid map of FIG. 11 which comprises a multiple cloning site that comprises the nucleotide sequence set forth in SEQ ID NO: 7.

Embodiment 48

A method for making a plasmid vector comprising cleaving the plasmid of any of embodiments 1 to 28 and ligating the ends of the cleaved plasmid to compatible ends of an introduced polynucleotide.

Embodiment 49

The method of embodiment 48, wherein the introduced polynucleotide encodes at least one of a short hairpin RNA for down-regulation of an HIV-1 co-receptor or encodes an HIV-1 fusion inhibitor.

Embodiment 50

A kit comprising (a) the lentiviral transfer vector plasmid of any of embodiments 1 to 28; and (b) packaging cell line cells.

Embodiment 51

The kit of embodiment 50, wherein the packaging cell line cells are selected from the group consisting of GPR, GPRG, GPRT, GPRTG, and a derivative thereof.

Embodiment 52

The kit of embodiment 50, further comprising a bleomycin resistance (ble) cassette.

Embodiment 53

A lentiviral vector derived from the plasmid of any of embodiments 1-28.

Embodiment 54

The lentiviral vector of embodiment 53, wherein the lentiviral vector comprises at least one additional nucleotide sequence.

Embodiment 55

The lentiviral vector of embodiment 54, wherein the at least one additional nucleotide sequence is selected from the group consisting of a nucleotide sequence which encodes a short hairpin RNA for down-regulation of an HIV-1 co-receptor and a nucleotide sequence which encodes an HIV-1 fusion inhibitor.

Embodiment 56

The lentiviral vector of embodiment 55, wherein the lentiviral vector is LVsh5/C46.

Embodiment 57

The lentiviral vector of embodiment 55, wherein the lentiviral vector comprises a sequence having at least 95% identity to that of SEQ ID NO: 8.

Embodiment 58

A cell comprising the lentiviral vector of any of embodiments 53 to 57.

Embodiment 59

A pharmaceutical composition comprising the lentiviral vector of any of embodiments 53-57 and a carrier.

All publications mentioned in this specification are herein incorporated by reference in their entirety. It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A recombinant plasmid comprising a nucleotide sequence having at least 90% identity to the sequence of SEQ ID NO: 1.

2. The recombinant plasmid of claim 1, wherein the nucleotide sequence has at least 95% identity to the sequence of SEQ ID NO: 1.

3. The recombinant plasmid of claim 1, wherein the recombinant plasmid comprises a multiple cloning site comprising BstBI, MluI, NotI, and ClaI restriction endonuclease sites.

4. The recombinant plasmid of claim 1, wherein the nucleotide sequence differs by not more than 100 nucleotides from the sequence of SEQ ID NO: 1.

5. The recombinant plasmid of claim 4, wherein the nucleotide sequence differs by not more than 50 nucleotides from the sequence of SEQ ID NO: 1.

6. A recombinant plasmid comprising a vector cassette having a nucleotide sequence having at least 90% identity to the sequence of SEQ ID NO: 2.

7. The recombinant plasmid of claim 6, wherein the nucleotide sequence of the vector cassette has at least 95% identity to the sequence of SEQ ID NO: 2.

8. The recombinant plasmid of claim 6, wherein the vector cassette is flanked by at least two restriction endonuclease sites, the at least two restriction endonuclease sites independently selected from the group consisting of sfiI and Bsu36I.

9. The recombinant plasmid of claim 6, wherein the recombinant plasmid comprises between about 6500 nucleotides and about 6750 nucleotides.

10. The recombinant plasmid of claim 6, wherein the recombinant plasmid comprises between about 6600 nucleotides and about 6700 nucleotides.

11. The recombinant plasmid of claim 6, wherein the vector cassette comprises a multiple cloning site including BstBI, MluI, NotI, and ClaI restriction endonuclease sites.

12. The recombinant plasmid of claim 6, wherein the recombinant plasmid further comprises a tetracycline repressible promoter upstream of the vector cassette.

* * * * *